United States Patent
Hiroshige et al.

(10) Patent No.: US 10,561,389 B2
(45) Date of Patent: Feb. 18, 2020

(54) RADIOGRAPHIC IMAGE CAPTURING APPARATUS AND RADIOGRAPHIC IMAGE CAPTURING SYSTEM

(71) Applicant: Konica Minolta, Inc., Chiyoda-ku, Tokyo (JP)

(72) Inventors: Akira Hiroshige, Kokubunji (JP); Wataru Matsushita, Hino (JP); Nobuyuki Miyake, Yokohama (JP); Hidetake Tezuka, Tachikawa (JP); Tetsu Hosoki, Koganei (JP); Tomonori Gido, Kawasaki (JP)

(73) Assignee: KONICA MINOLTA, INC., Tokyo (JP)

( * ) Notice: Subject to any disclaimer, the term of this patent is extended or adjusted under 35 U.S.C. 154(b) by 270 days.

(21) Appl. No.: 15/528,930

(22) PCT Filed: Oct. 19, 2015

(86) PCT No.: PCT/JP2015/079394
§ 371 (c)(1),
(2) Date: May 23, 2017

(87) PCT Pub. No.: WO2016/084517
PCT Pub. Date: Jun. 2, 2016

(65) Prior Publication Data
US 2017/0311920 A1 Nov. 2, 2017

(30) Foreign Application Priority Data
Nov. 27, 2014 (JP) .................................. 2014-239692

(51) Int. Cl.
*A61B 6/00* (2006.01)

(52) U.S. Cl.
CPC .............. *A61B 6/54* (2013.01); *A61B 6/4266* (2013.01); *A61B 6/4405* (2013.01); *A61B 6/563* (2013.01)

(58) Field of Classification Search
None
See application file for complete search history.

(56) References Cited

U.S. PATENT DOCUMENTS

| 2009/0022276 A1 | 1/2009 | Ohara |
| 2013/0058456 A1* | 3/2013 | Kuwabara ............ A61B 6/4233 378/62 |

(Continued)

FOREIGN PATENT DOCUMENTS

| JP | 2005204860 A | 8/2005 |
| JP | 2010137059 A | 6/2010 |

(Continued)

OTHER PUBLICATIONS

International Search Report corresponding to Application No. PCT/JP2015/079394; dated Dec. 28, 2015.

(Continued)

*Primary Examiner* — Hoon K Song
(74) *Attorney, Agent, or Firm* — Cantor Colburn LLP

(57) ABSTRACT

A radiographic image capturing apparatus includes: a two-dimensional array of radiation detecting elements that generate one or more electric charges in proportion to a dose of incident radiation; and a control unit that performs control, at least, to read the electric charges from the radiation detecting elements and generate image data. An image capturing mode is switchable between a controlled mode in which the radiographic image capturing apparatus is under control of an external console and a stand-alone mode in which the radiographic image capturing apparatus autonomously performs image capturing without the control of the console. When the image capturing mode is switched to the controlled mode or the stand-alone mode, the control unit changes its own process so as to meet the switched image capturing mode.

11 Claims, 12 Drawing Sheets

(56) References Cited

U.S. PATENT DOCUMENTS

| | | | |
|---|---|---|---|
| 2014/0254758 A1* | 9/2014 | Saigusa | A61B 6/545 378/62 |
| 2014/0254759 A1* | 9/2014 | Haraguchi | G01N 23/04 378/62 |
| 2016/0022231 A1 | 1/2016 | Nonaka | |

FOREIGN PATENT DOCUMENTS

| | | |
|---|---|---|
| JP | 2011254971 A | 12/2011 |
| JP | 2014166556 A | 9/2014 |
| JP | 2014171542 A | 9/2014 |
| WO | 2011142157 A1 | 11/2011 |

OTHER PUBLICATIONS

International Preiiminary Report an Patentability including Written Opinion of the International Searching Authority corresponding to Application No. PCT/JP2015/079394; dated May 30, 2017.

Extended European Search Report corresponding to Application No. 15863347.9-1124/3225163 PCT/JP2015079394; dated Jul. 3, 2018.

JPO Notice of Reasons for Refusal corresponding to Application No. 2016-561452; dated Jul. 23, 2019.

JPO Notice of Reasons for Refusal corresponding to Application No. 2016-561452; dated Dec. 3, 2019.

* cited by examiner

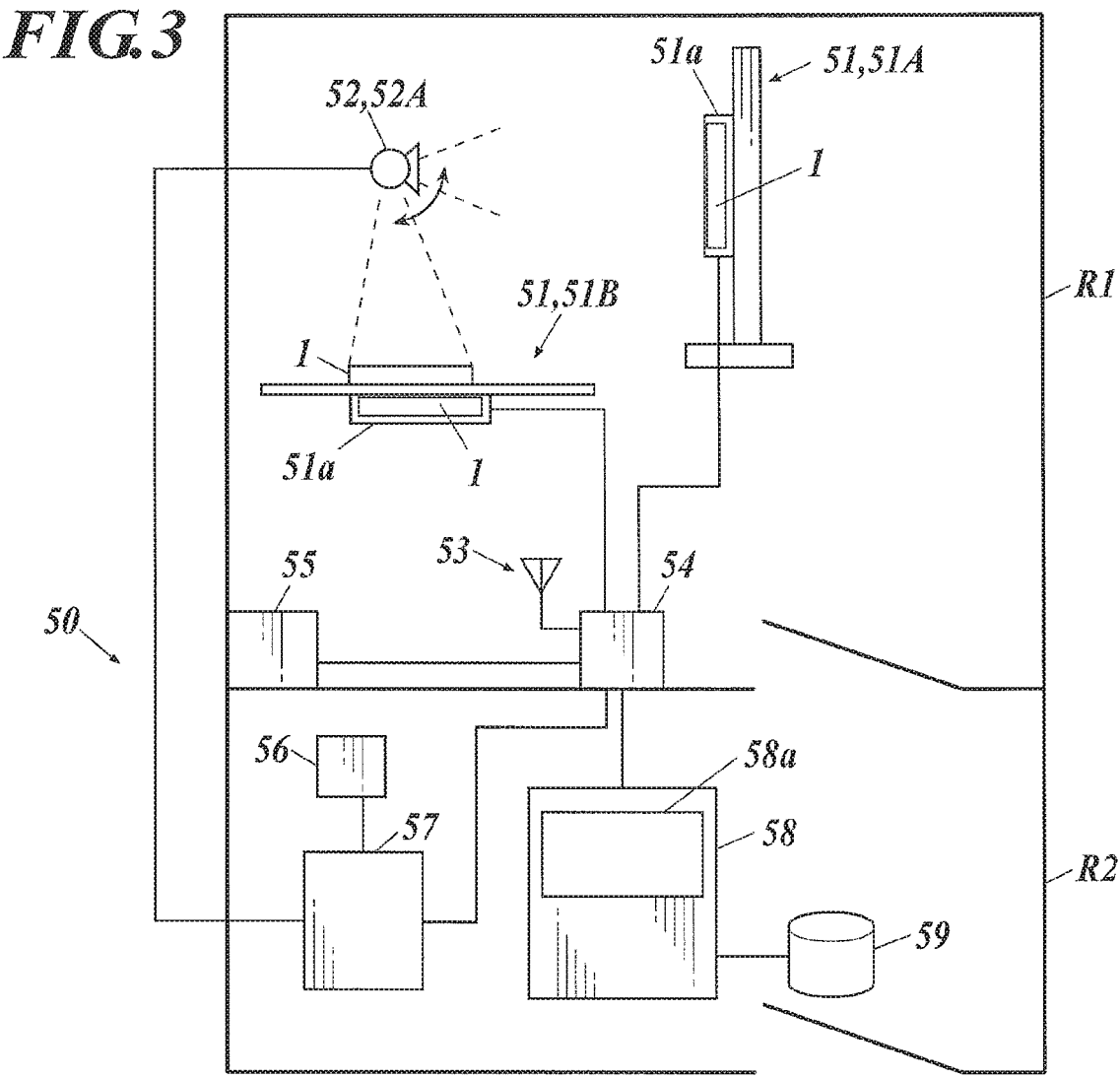
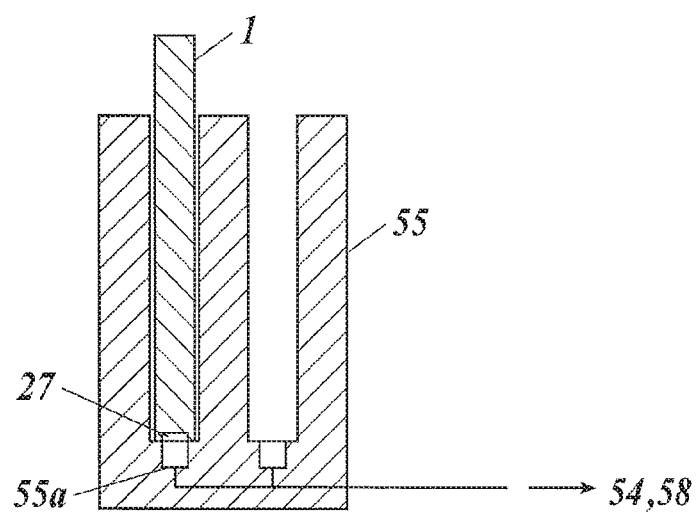

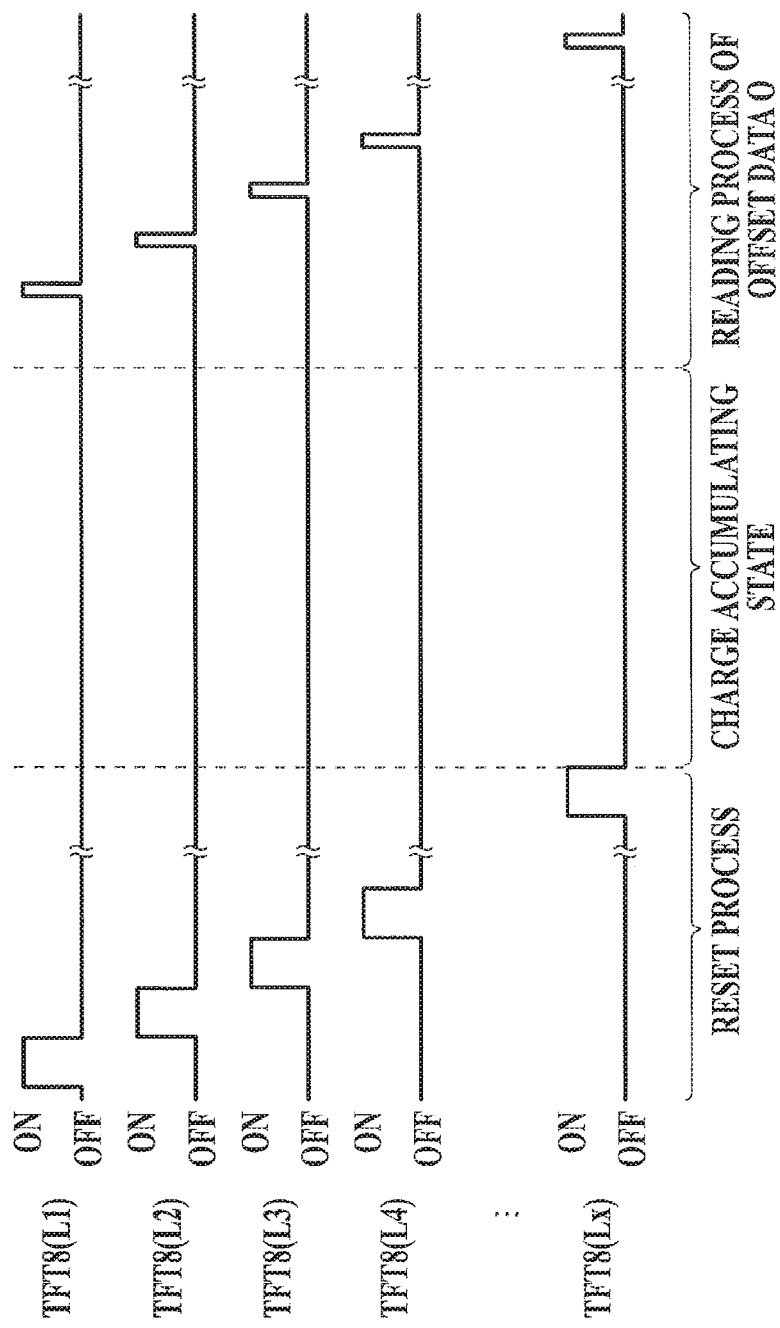

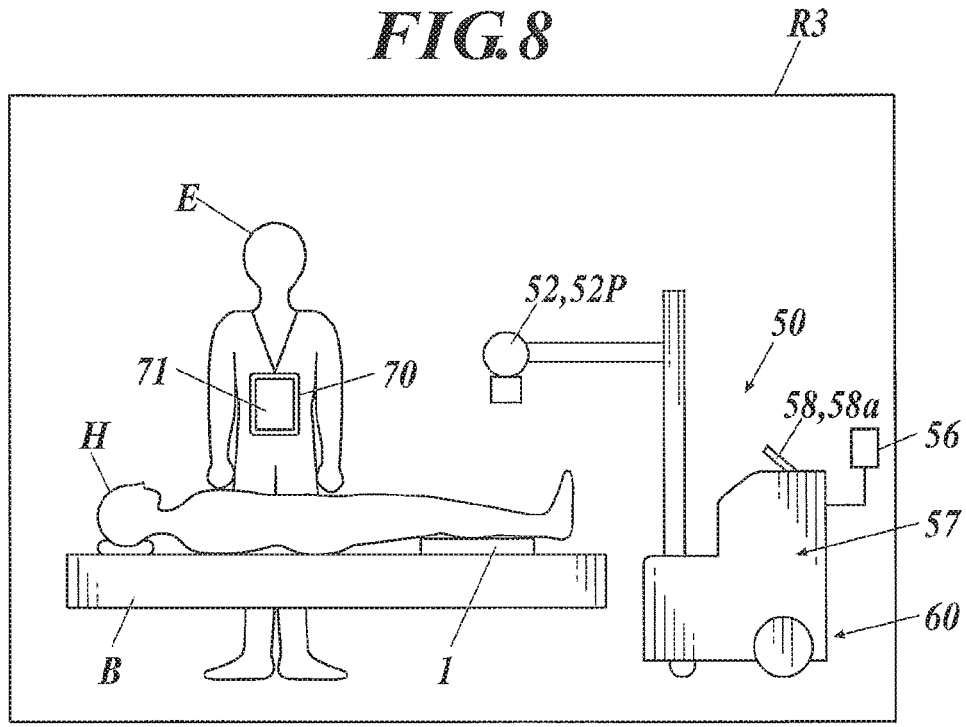

| P1 | P2 | P3 | P4 | P5 | P6 | P7 | P8 | P9 |
|---|---|---|---|---|---|---|---|---|
| CAPTURING ORDER ID | PATIENT ID | PATIENT NAME | SEX | AGE | CLINICAL DEPARTMENT | CAPTURING SITE | CAPTURING DIRECTION | BODY POSITION |
| 001 | 100085 | A | MALE | 25 | SURGERY | FULL LEG | R FRONT | UPRIGHT POSITION |
| 002 | 100320 | B | FEMALE | 15 | ORTHOPEDIC SURGERY | LEG | L FRONT | RECUMBENT POSITION |
| 003 | 100325 | C | MALE | 60 | ORTHOPEDIC SURGERY | HAND | L | RECUMBENT POSITION |
| 004 | 100085 | A | MALE | 25 | SURGERY | CHEST | FRONT | UPRIGHT POSITION |
| 005 | 100085 | A | MALE | 25 | SURGERY | CERVICAL SPINE | SIDE R → L | UPRIGHT POSITION |
| 006 | 100085 | A | MALE | 25 | SURGERY | ABDOMEN | FRONT | RECUMBENT POSITION |

RADIOGRAPHIC IMAGE CAPTURING APPARATUS AND RADIOGRAPHIC IMAGE CAPTURING SYSTEM

CROSS REFERENCE TO RELATED APPLICATIONS

This is the U.S. national stage of application No. PCT/JP2015/079394, filed Oct. 19, 2015. Priority under 35 U.S.C. § 119(a) and 35 U.S.C. § 365(b) is claimed from Japanese Application No. 2014-239692, filed Nov. 27, 2014, the disclosure of which is incorporated herein by references.

TECHNICAL FIELD

The present invention relates to a radiographic image capturing apparatus and a radiographic image capturing system, in specific a radiographic image capturing apparatus and a radiographic image capturing system for radiography.

BACKGROUND ART

Various radiographic image capturing apparatuses (flat panel detectors) have been developed that each includes a two-dimensional array of radiation detecting elements and reads electric charges generated in the radiation detecting elements in proportion to radiation emitted from a radiation irradiating apparatus and passing through a subject. Such radiographic image capturing apparatuses are used for image capturing in medical facilities, such as a hospital. A portable radiographic image capturing apparatus has been developed and put to practical use that includes a casing accommodating a sensor panel provided with radiation detecting elements and the like.

A traditional portable radiographic image capturing apparatus is operated under image capturing control by a console composed of, for example, a computer. In detail, the console carries out several processes, such as startup of the radiographic image capturing apparatus, switch of power consuming states (low-consumption state (sleep state) and image-capturing state (wake-up state)) of the radiographic image capturing apparatus, transfer of image data from the radiographic image capturing apparatus after every capturing operation, and correlation (linkage) of generated radiographic images with capturing order information containing instructions as to the capturing of the radiographic images (refer to PTL 1, for example).

The image capturing mode of the radiographic image capturing apparatus under the control of an external console is referred to as a controlled mode. In specific, the controlled mode represents a normal image capturing mode for traditional image capturing by the radiographic image capturing apparatus under image capturing control by the console.

Another type of radiographic image capturing apparatus, such as that disclosed in PTL 2, is recently known that performs image capturing without the control of a console and stores image data of the captured images in a storage unit provided in the radiographic image capturing apparatus. PTL 2 discloses a downloading process of captured image data from the radiographic image capturing apparatus to the console (controller in PTL 2) by connection of a cable to the radiographic image capturing apparatus or connection of a storage unit detached from the radiographic image capturing apparatus to the console.

The image capturing mode of the radiographic image capturing apparatus in a stand-alone state without the control of a console is referred as a stand-alone mode. In specific, the stand-alone mode represents an image capturing mode in which the radiographic image capturing apparatus performs image capturing without image capturing control by the console and stores the captured image data in the radiographic image capturing apparatus.

CITATION LIST

Patent Literature

PTL 1: International Publication WO2011/142157
PTL 2: Japanese Patent Application Laid-Open Publication No. 2010-137059

SUMMARY OF INVENTION

Problems to be Solved by Invention

In the controlled mode, the radiographic image capturing apparatus usually receives capturing order information on respective image capturing operations to be performed from the console and performs image capturing operations in sequence in accordance with the capturing order information. Image data of the captured images are transferred from the radiographic image capturing apparatus to the console in the order of image capturing. In this way, the correspondence between the radiographic images generated on the basis of the image data from the console as described above and the capturing order information can be certainly established, without false correspondence between the radiographic images and capturing order information irrelevant to the captured radiographic images, for example.

Unfortunately, if the operator or radiologist performs an additional image capturing not included in the capturing order information, the order of the generated radiographic images will be shifted by one from the order of the capturing order information and thus the console fails to establish the correct correspondence between the radiographic images and the capturing order information in the subsequent image capturing. Thus, the radiographic image capturing apparatus cannot perform an additional image capturing irrelevant to the capturing order information in the controlled mode.

Alternatively, the additional image capturing may be performed after a new capturing order information corresponding to the additional image capturing is prepared and stored in the console, for example. Unfortunately, this is a troublesome process for the operator or radiologist.

The operator or radiologist can freely perform image capturing with the radiographic image capturing apparatus in the stand-alone mode without the control of the console or restrictions based on the capturing order information. Thus, the operator or radiologist can discretionally perform the additional image capturing. Thus, the radiographic image capturing apparatus in the stand-alone mode is easy to use by the operator or radiologist from at least this viewpoint.

The radiographic image capturing apparatus in the stand-alone mode can freely perform image capturing without any restrictions based on the capturing order information. Thus, the radiologist or medical worker needs to establish correspondence between the radiographic images generated on the basis of the captured image data and the capturing order information with the console. The radiographic image capturing apparatus in the stand-alone mode is inconvenient for the medical worker or radiologist from at least this viewpoint.

Means for Solving Problems

An object of the present invention, which has been accomplished to solve the above problems, is to provide a radiographic image capturing apparatus and a radiographic image capturing system that have different advantages in the controlled and stand-alone image capturing modes.

To solve the above problems, a radiographic image capturing apparatus of the present invention includes: a two-dimensional array of radiation detecting elements that generate one or more electric charges in proportion to a dose of incident radiation; and a control unit that performs control, at least, to read the electric charges from the radiation detecting elements and generate image data. An image capturing mode is switchable between a controlled mode in which the radiographic image capturing apparatus is under control of an external console and a stand-alone mode in which the radiographic image capturing apparatus autonomously performs image capturing without the control of the console. When the image capturing mode is switched to the controlled mode or the stand-alone mode, the control unit changes its own process so as to meet the switched image capturing mode.

A radiographic image capturing system of the present invention includes: a radiographic image capturing apparatus including: a two-dimensional array of radiation detecting elements that generate one or more electric charges in proportion to a dose of incident radiation; and a control unit that performs control, at least, to read the electric charges from the radiation detecting elements and generate image data; and a console capable of controlling an operation of the radiographic image capturing apparatus. The radiographic image capturing apparatus is capable of switching an image capturing mode between a controlled mode in which the radiographic image capturing apparatus is under control of the console and a stand-alone mode in which the radiographic image capturing apparatus autonomously performs image capturing without the control of the console. When the image capturing mode is switched to the controlled mode or the stand-alone mode, the control unit of the radiographic image capturing apparatus changes its own process so as to meet the switched image capturing mode.

The radiographic image capturing apparatus and the radiographic image capturing system according to the present invention can achieve different advantages in the controlled and stand-alone image capturing modes of the radiographic image capturing apparatus.

BRIEF DESCRIPTION OF THE DRAWINGS

FIG. 3 illustrates a configurational example of a radiographic image capturing system installed in an image capturing room.

FIG. 4 is a cross-sectional view of the radiographic image capturing apparatus placed in a cradle with connection between connectors.

FIG. 7 is a timing chart illustrating the processing sequence in FIG. 6 being repeated to read offset data.

FIG. 8 illustrates a configurational example of a radiographic image capturing system installed in a mobile medical cart.

FIG. 9 illustrates example capturing order information.

MODES FOR CARRYING OUT THE INVENTION

A radiographic image capturing apparatus and a radiographic image capturing system according to embodiments of the present invention will now be described with reference to the drawings.

The radiographic image capturing apparatus according to this embodiment is an indirect radiographic image capturing apparatus including a scintillator that converts incident radiation into light having different wavelengths, such as visible light, and radiation detecting elements that acquire image data. Alternatively, the radiographic image capturing apparatus of the present invention may be a direct radiographic image capturing apparatus that directly detects incident radiation with the radiation detecting elements without a scintillator.

[Radiographic Image Capturing Apparatus]

Figure 1:
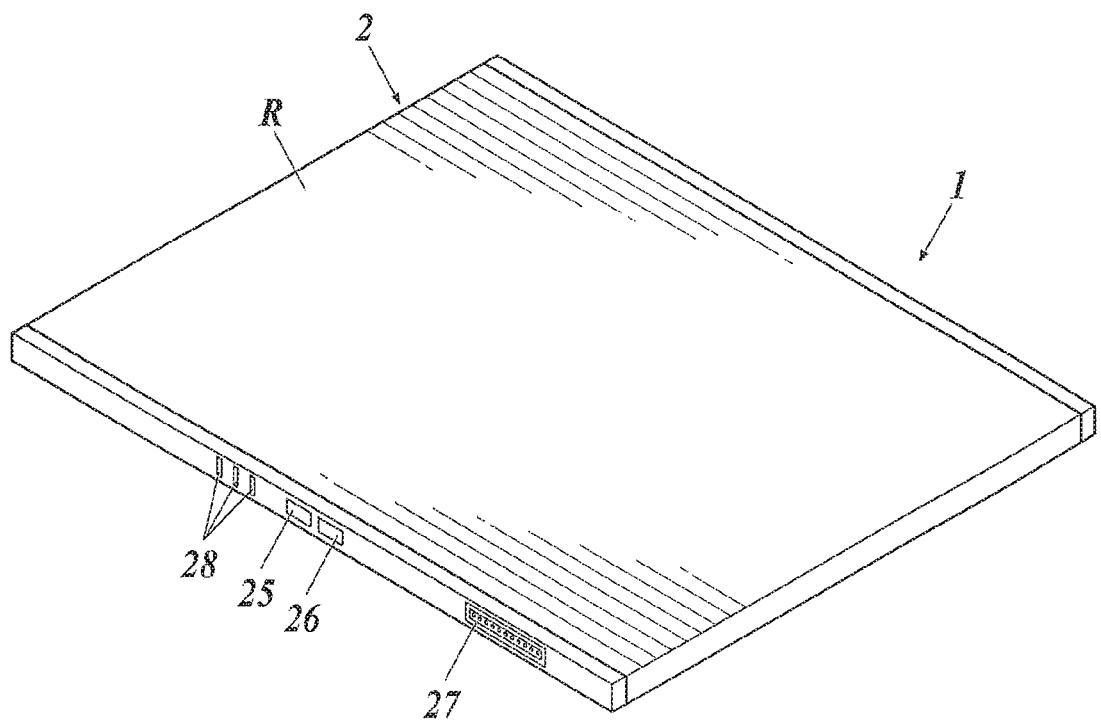
FIG. 1 is an external perspective view of a radiographic image capturing apparatus according to an embodiment.

The basic configuration of the radiographic image capturing apparatus according to this embodiment will now be described. FIG. 1 is an external perspective view of the radiographic image capturing apparatus.

A radiographic image capturing apparatus 1 according to this embodiment includes a casing 2 accommodating radiation detecting elements 7 described below. The casing 2 is provided with a power switch 25, a selection switch 26, a connector 27, and an indicator 28 on its one side face. Although not illustrated, the casing 2 according to this embodiment is provided with an antenna 29 (see FIG. 2) for wireless communication with a console 58 described below on the opposite side face, for example. The radiographic image capturing apparatus 1 establishes wireless communication with an external unit through the antenna 29 and wire communication with an external unit through a cable (not shown) connected to the connector 27.

Figure 2:
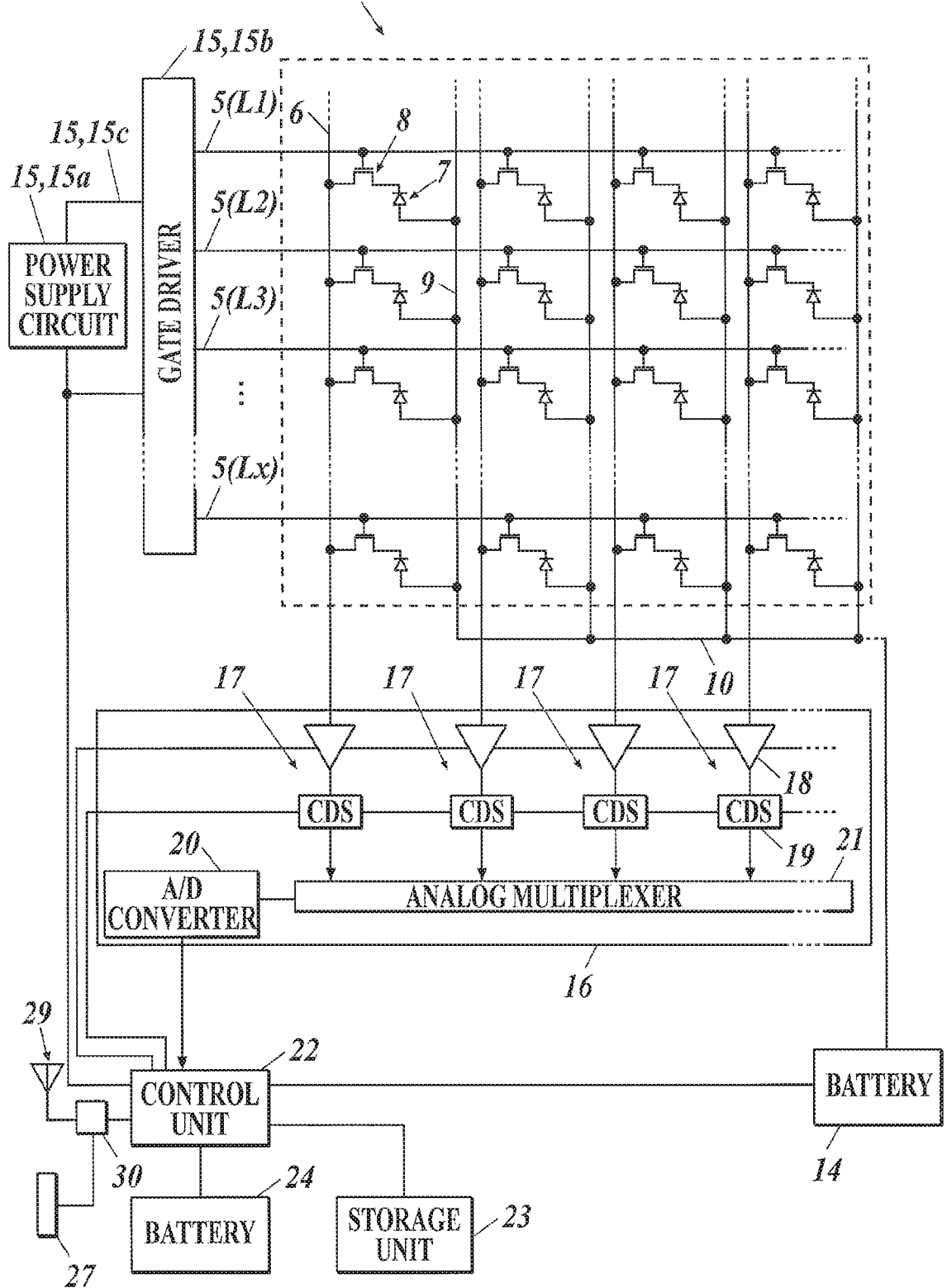
FIG. 2 is a block diagram illustrating an equivalent circuit of the radiographic image capturing apparatus.

FIG. 2 is a block diagram illustrating an equivalent circuit of the radiographic image capturing apparatus. With reference to FIG. 2, the radiographic image capturing apparatus 1 includes a two-dimensional array (matrix) of the radiation detecting elements 7 disposed on a sensor substrate (not shown). The radiation detecting elements 7 each generates electric charges in proportion to the doses of incident radiation. The radiation detecting elements 7 are connected to bias lines 9, which are connected to a connection line 10. The connection line 10 is connected to a bias power supply 14. A reverse bias voltage is applied to each radiation detecting element 7 from the bias power supply 14 through the bias lines 9.

The radiation detecting elements 7 are connected to respective thin film transistors (TFTs) 8 as switching elements. The TFTs 8 are connected to a corresponding signal line 6. In a scan driving unit 15, a power supply circuit 15a supplies ON and OFF voltages to a gate driving unit 15b via a line 15c. The gate driver 15b switches the received voltage, and the switched voltage is applied to scanning lines 5(L1) to 5(Lx). The TFTs 8 are turned on in response to an ON voltage applied through the scanning lines 5 and cause the electric charges accumulated in the radiation detectors 7 to be discharged through the signal lines 6. The TFTs 8 are turned off in response to an OFF voltage applied through the scanning lines 5 to disconnect the radiation detecting elements 7 and the respective signal lines 6 and cause accumulation of the electric charges in the radiation detecting elements 7.

A readout IC 16 includes multiple readout circuits 17, which are connected to the respective signal lines 6. During generation of image data D, the electric charges in the radiation detecting elements 7 are discharged to the respective readout circuits 17 through the respective signal lines 6, and voltage values corresponding to the electric charges are output from amplifier circuits 18. Correlated double sampling circuits ("CDSs" in FIG. 2) 19 read the voltage values from the amplifier circuits 18 and output analog image data D to the downstream components. The image data D are sequentially sent to an A/D converter 20 via an analog multiplexer 21, converted to digital image data D at the A/D converter 20, and then output to and stored in a storage unit 23.

A control unit 22 includes a computer (not shown) provided with a central processing unit (CPU), a read only memory (ROM), a random access memory (RAM), and an input/output interface which are connected to a bus, and a field programmable gate array (FPGA). The control unit 22 may be composed of a dedicated control circuit. The control unit 22 is connected to the storage unit 23 provided with a static RAM (SRAM) or a synchronous DRAM (SDRAM), and a communication device 30 that establishes wireless or wired communication with external units via the antenna 29 or the connector 27.

The control unit 22 is connected to a battery 24 that supplies necessary electrical power to the functional components, such as the scan driving unit 15, the readout circuits 17, the storage unit 23, and the bias power supply 14. The control unit 22 controls the operation of the scan driving unit 15, the readout circuits 17, and other components as described above to read the electric charges from the radiation detecting elements 7 and generate the image data D.

The radiographic image capturing apparatus 1 according to this embodiment can be installed on a photography platform 51 for image capturing. Although not illustrated, the radiographic image capturing apparatus 1 may alternatively be used in a stand-alone state without the photography platform 51 to capture images of a subject or patient by placing the apparatus in contact with the patient or between the patient and the bed, for example.

[Radiographic Image Capturing System]

Before detailed description of the radiographic image capturing apparatus according to this embodiment, a configurational example of the radiographic image capturing system including the radiographic image capturing apparatus 1 will now be described. FIG. 3 illustrates a configurational example of the radiographic image capturing system 50 installed in an image capturing room R1.

Radiography platforms 51 are placed in the image capturing room R1. The radiography platforms 51 each include a cassette holder 51a in which the radiographic image capturing apparatus 1 can be loaded. FIG. 3 illustrates the two radiography platforms 51: a photography platform 51A for image capturing in an upright position and a photography platform 51B for image capturing in a recumbent position. Alternatively, either one of the two radiography platforms 51 may be provided. With reference to FIG. 3, the image capturing room R1 is provided with at least one radiation source 52A of a radiation irradiating apparatus 57 that emits radiation through the subject to the radiographic image capturing apparatus 1 installed on the photography platform 51.

The image capturing room R1 is provided with a repeater 54 including an access point 53 for relaying the communication between individual units inside the image capturing room R1 and individual units outside the image capturing room R1. The repeater 54 is connected to the radiation irradiating apparatus 57 and the console 58. The repeater 54 includes a converter (not shown) for converting local area network (LAN) communication signals sent from the radiographic image capturing apparatus 1 and the console 58 to the radiation irradiating apparatus 57 into signals for the radiation irradiating apparatus 57, and converting the signals for the radiation irradiating apparatus 57 into LAN communication signals.

The image capturing room R1 is provided with a cradle 55. Alternatively, the cradle 55 may be disposed in a front chamber R2 described below. With reference to FIG. 4, the radiographic image capturing apparatus 1 is placed in the cradle 55 to connect the connector 27 (see FIG. 1) of the radiographic image capturing apparatus 1 and the connector 55a of the cradle 55, so as to supply electric power from the cradle 55 to the battery 24 (see FIG. 2) of the radiographic image capturing apparatus 1, to charge the battery 24.

The repeater 54 is connected to the cradle 55 as illustrated in FIG. 3, and the radiographic image capturing apparatus 1 residing in the image capturing room R1 is placed in the cradle 55 as illustrated in FIG. 4, so as to send a cassette ID as identification information of the radiographic image capturing apparatus 1 to the console 58 via the repeater 54. In this way, the console 58 may be configured to manage the radiographic image capturing apparatus 1 residing in the image capturing room R1.

Figure 5A:
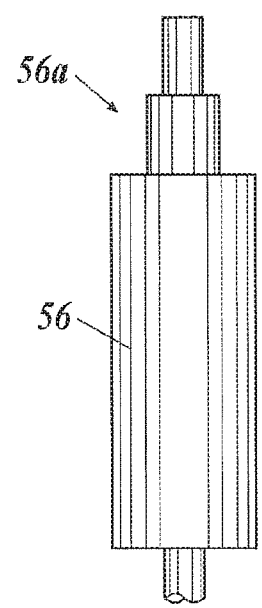
FIG. 5A illustrates an exposure switch of a radiation irradiating apparatus.
Figure 5B:
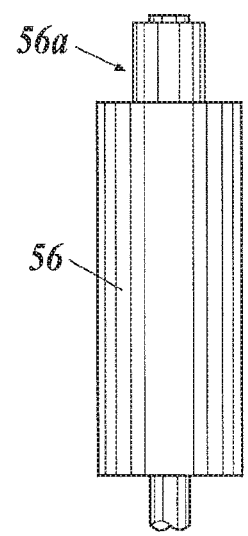
FIG. 5B illustrates a button of the exposure switch in a half-pressed state.
Figure 5C:
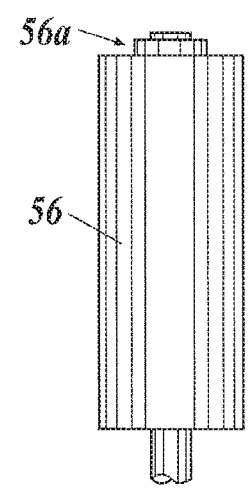
FIG. 5C illustrates the button of the exposure switch in a full-pressed state.

The front chamber (operating chamber) R2 is provided with an operator station of the radiation irradiating apparatus 57. The operator station includes an exposure switch 56 as illustrated in FIG. 5A. In response to a first-step operation (i.e. so-called half-pressing operation) performed by the operator or radiologist to the button 56a of the exposure switch 56 as illustrated in FIG. 5B, the radiation irradiating apparatus 57 activates the radiation source 52. In response to a second-step operation (i.e. so-called full-pressing operation) performed by the operator to the button 56a of the exposure switch 56 as illustrated in FIG. 5C, the radiation irradiating apparatus 57 instructs the radiation source 52 to emit radiation.

In detail, the full-pressing of the exposure switch 56 by the operator instructs the radiation irradiating apparatus 57 to send a radiation start signal to the radiographic image capturing apparatus 1. At this point, the radiographic image capturing apparatus 1 carries out pre-processing for image capturing or resetting of the radiation detecting elements 7 through sequential application of an ON voltage from the gate driver 15b of the scan driving unit 15 (see FIG. 2) to the scanning lines 5(L1) to 5(Lx). Upon reception of the radiation start signal from the radiation irradiating apparatus 57, the radiographic image capturing apparatus 1 halts the resetting process, as illustrated in FIG. 6.

The gate driver 15b applies an OFF voltage to the scanning lines 5(L1) to 5(Lx) to turn off all the TFTs 8 such that the radiographic image capturing apparatus 1 enters a charge accumulating state in which the electric charges generated in response to incident radiation are accumulated in the radiation detecting elements 7, and the radiographic image capturing apparatus 1 sends an interlock release signal to the radiation irradiating apparatus 57. Upon reception of the interlock release signal, the radiation irradiating apparatus 57 emits radiation from the radiation source 52.

Figure 6:
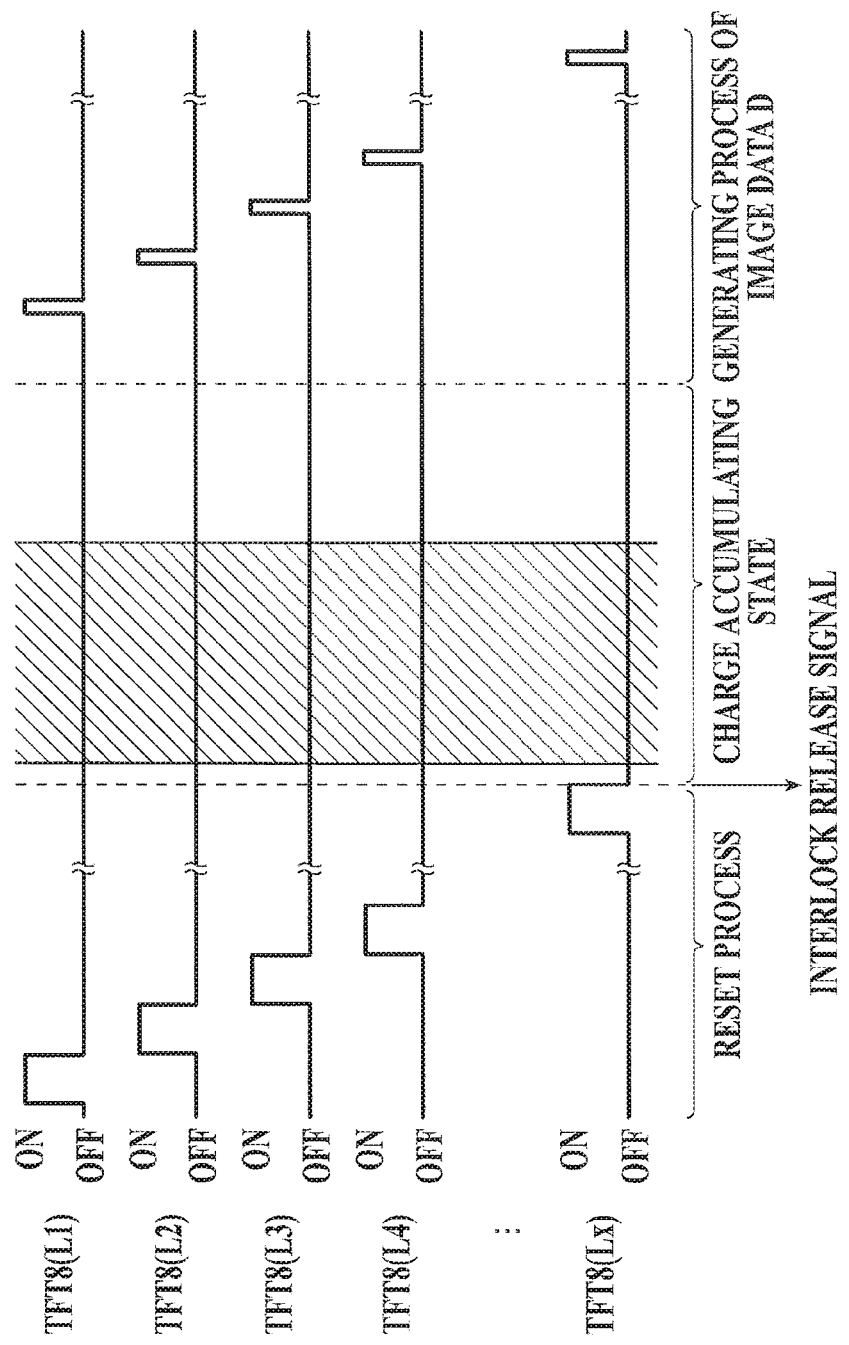
FIG. 6 is a timing chart illustrating the timing of application of an ON voltage to scanning lines during image capturing by the radiographic image capturing apparatus in cooperation with the radiation irradiating apparatus.

The hatched area in FIG. 6 represents the period of radiation irradiation. Upon completion of radiation irradiation, the control unit 22 of the radiographic image capturing apparatus 1 instructs the gate driver 15b to sequentially apply an ON voltage to the scanning lines 5(L1) to 5(Lx) and reads the electric charges from the radiation detecting elements 7, to generate image data D.

The control unit 22 of the radiographic image capturing apparatus 1, which is not irradiated with radiation before or after image capturing, repeats the same voltage application sequence as that illustrated in FIG. 6 to read offset data O, as illustrated in FIG. 7. The offset data O is equivalent to the offset caused by dark charges (also referred to as dark current) superposed to the image data D generated as described above. In the subsequent image correction process, the true image data $D^*$ (where $D^*=D-O$) corresponding only to the electric charges generated in response to incident radiation can be determined by subtracting the offset data O from the image data D for every radiation detecting element 7.

With reference to FIG. 3, the front chamber R2 is provided with the console 58 composed of a computer. The console 58 is provided with a display unit 58a including a cathode ray tube (CRT) or a liquid crystal display (LCD) and an input unit (not shown), such as a mouse and a keyboard. The console 58 is connected to an external or internal storage unit 59 including a hard disk drive (HDD).

Although not illustrated, the console 58 is connected to external systems, such as a hospital information system (HIS), a radiology information system (RIS), and/or a picture archiving and communication system (PACS), via any network, such as a LAN.

FIG. 3 illustrates one image capturing room R1 corresponding to one console 58. Alternatively, a facility, such as a hospital, may be provided with multiple image capturing rooms corresponding to one or more consoles via a network (not shown).

The radiographic image capturing system 50 may be configured not only in an image capturing room, as illustrated in FIG. 3, but also in a mobile medical cart 60, as illustrated in FIG. 8, for example. The radiographic image capturing apparatus 1, which is carried into a hospital room R3 or the home of a patient H together with the mobile medical cart 60, is disposed between the bed B or mattress and the body of the patient H or in contact with the body of the patient H, as illustrated in FIG. 8, for example.

Radiation from the radiation source 52P of the radiation irradiating apparatus 57 loaded on the mobile medical cart 60 passes through the body of the patient H or subject and is incident on the radiographic image capturing apparatus 1. The mobile medical cart 60 may be provided with the console 58 composed of a notebook computer and the like. Alternatively, the mobile medical cart 60 may not be provided with the console 58, as described below. Although omitted in FIG. 8, the mobile medical cart 60 is also appropriately provided with the access point 53 and the repeater 54, as illustrated in FIG. 3.

Alternatively, the operator E or radiologist may carry a portable information terminal 70 including a display unit 71 so as to confirm images on the display unit 71, as illustrated in FIG. 8. This configuration may also be applied to image capturing performed in the image capturing room R1, as illustrated in FIG. 3. This configuration will be described below.

For image capturing performed in the image capturing room R1 as described above, the radiographic image capturing apparatus 1 and the radiation irradiating apparatus 57 usually cooperate with each other by transmitting radiation start signals and interlock release signals. The radiation irradiating apparatus 57 loaded in the mobile medical cart 60 may intentionally or unintentionally fail to cooperate with the radiographic image capturing apparatus 1 in image capturing. In such the case, the radiation irradiating apparatus 57 is configured to immediately emit radiation in response to the full-pressing of the exposure switch 56 by the operator, as described above.

In such a case, in order to accumulate in the radiation detecting elements 7 the electric charges generated in response to radiation irradiation as described above, the radiographic image capturing apparatus 1 needs to turn off all the TFTs 8 at the time of start of the radiation irradiation so as to enter the charge accumulating state. Thus, the radiographic image capturing apparatus 1 is often configured to detect the start of radiation irradiation by itself. Alternatively, the radiographic image capturing apparatus 1 may be configured to repeat the generation process of the image data D described above from before the start of radiation irradiation and add up the image data of every frame, to restore the image data for the corresponding radiation detecting elements 7.

The radiographic image capturing apparatus 1 may detect the start of radiation irradiation in accordance with any method. Examples of such a method include those disclosed in Japanese Patent Application Laid-Open Publication No. 2009-219538, International Publications WO2011/135917 and WO2011/152093, and other known methods.

The cooperation between the radiographic image capturing apparatus 1 and the radiation irradiating apparatus 57 has no direct connection to the controlled mode and the stand-alone mode of the radiographic image capturing apparatus 1. That is, the radiographic image capturing apparatus 1 operates in the controlled image capturing mode during image capturing under the control of the console 58, whereas the radiographic image capturing apparatus 1 operates in the stand-alone image capturing mode during autonomous image capturing, i.e., image capturing without the control of the console 58, regardless of the cooperation between the radiographic image capturing apparatus 1 and the radiation irradiating apparatus 57.

[Controlled Mode and Stand-Alone Mode of Radiographic Image Capturing Apparatus]

The controlled mode and the stand-alone mode of the radiographic image capturing apparatus 1 according to this embodiment and the configuration of the radiographic image capturing apparatus 1 inherent in this embodiment will now be described. The operation of the radiographic image capturing apparatus 1 according to this embodiment will also be described.

As described above, the radiographic image capturing apparatus 1 operates under the control of the console 58 (see FIG. 3) as in traditional radiographic image capturing apparatuses. The image capturing mode of the radiographic image capturing apparatus 1 operating under the control of the console 58 is referred to as the controlled mode in the present invention.

In the controlled mode, the control unit 22 of the radiographic image capturing apparatus 1 (see FIG. 2) starts pre-processing for image capturing in response to a signal instructing the start of image capturing from the console 58, for example, the pre-processing including initiation of the functional units, such as the scan driving unit 15, and start of the resetting process of the radiation detecting elements 7 to remove electric charges remaining in the radiation detecting elements 7. In several cases, capturing order information on the image capturing to be performed may be sent from the console 58 at the time of instructing the start of image capturing.

In response to a wake-up signal from the console 58, for example, the control unit 22 of the radiographic image capturing apparatus 1 shifts the power consumption state from a low-consumption state to an image-capturing state, to apply a reverse bias voltage from the bias power supply 14 to the radiation detecting elements 7 through the bias lines 9 or start a detection process of the start of radiation irradiation if the radiographic image capturing apparatus 1 is configured to detect the start of radiation irradiation by itself, as described above.

After generation of the image data D (see FIG. 6) or reading of the offset data O as described above, the control unit 22 of the radiographic image capturing apparatus 1 immediately transfers the image data D or the offset data O to the console 58. In some cases, before transfer of the image data D, extraction of a portion of the image data D or lossy compression of the image data D may be performed and the resulting data may be sent to the console 58, to display a confirmation preview image on the display unit 58a of the console 58, as is well known.

If a subsequent image capturing is to be carried out, the control unit 22 of the radiographic image capturing apparatus 1 resumes the pre-possessing for the subsequent image capturing such as resetting of the radiation detecting elements 7. If a subsequent image capturing is not to be performed, the power consumption state shifts, automatically or in response to an instruction from the console 58, from the image-capturing state to the low-consumption state.

In the controlled mode, the control unit 22 of the radiographic image capturing apparatus 1 carries out its own process under the control of the console 58, and precisely controls the operation of the functional units, such as the scan driving unit 15 and the readout circuits 17.

The capturing order information is information assigning the target patient, the site to be captured, and the image capturing direction, etc. of the image capturing. For example, the capturing order information contains patient information consisting of "patient ID" P2, "patient name" P3, "sex" P4, "age" P5, and "clinical department" P6, and capturing conditions consisting of "capturing site" P7, "capturing direction" P8, and "body position" P9, as illustrated in FIG. 9, for example. "Capturing order IDs" P1 are automatically assigned to the corresponding capturing order information, for example, in the order of reception of the capturing order information. The console 58 obtains the capturing order information from the HIS or the RIS in response to a predetermined operation by the operator or radiologist.

Alternatively, the radiographic image capturing apparatus 1 can be configured to perform image capturing in a stand-alone state without control by the console 58, as described above. In such the case, the radiographic image capturing apparatus 1 is often not in communication with the console 58. Thus, the captured image data D is often stored in the radiographic image capturing apparatus 1, specifically in the storage unit 23 (see FIG. 2). This image capturing mode of the radiographic image capturing apparatus 1 without control by the console 58 is referred to as the stand-alone mode in the present invention.

In the stand-alone mode, upon turning-on of the power supply in response to operation of the power switch 25 (see FIG. 1) by the operator or radiologist, for example, the control unit 22 of the radiographic image capturing apparatus 1 starts pre-processing for image capturing including initiation of the functional units, such as the scan driving unit 15, and start of the resetting process of the radiation detecting elements 7 for removal of electric charges remaining in the radiation detecting elements 7. In the stand-alone mode, communication is not established between the radiographic image capturing apparatus 1 and the console 58, as described above. Thus, the radiographic image capturing apparatus 1 does not preliminarily receive capturing order information on the image capturing to be performed. Alternatively, the operator or radiologist may input the capturing order information.

In response to operation of the selection switch 26 (see FIG. 1) by the operator or radiologist, for example, the control unit 22 of the radiographic image capturing apparatus 1 shifts the power consumption state from a low-consumption state to an image-capturing state, to apply a reverse bias voltage from the bias power supply 14 to the radiation detecting elements 7 through the bias lines 9 or start a detection process of the start of radiation irradiation if the radiographic image capturing apparatus 1 is configured to detect the start of radiation irradiation by itself, as described above, for example.

The control unit 22 of the radiographic image capturing apparatus 1 stores the generated image data D in the storage unit 23, and transfers the image data D to the console 58 upon establishment of wireless or wired communication with the console 58, as described above.

Upon completion of the image capturing and generation of image data D (see FIG. 6), the control unit 22 of the radiographic image capturing apparatus 1 resets the radiation detecting elements 7 to prepare for the subsequent image capturing, or detects the start of radiation irradiation if the radiographic image capturing apparatus 1 is configured to detect the start of radiation irradiation by itself.

After the generation of the image data D, the control unit 22 of the radiographic image capturing apparatus 1 shifts the power consumption state from the image-capturing state to the low-consumption state in response to the operation of the selection switch 26 by the operator or radiologist, for example. If subsequent image capturing is not performed for a predetermined time after the completion of the generation of the image data D (i.e., if a radiation start signal is not sent from the radiation irradiating apparatus 57 or if the start of radiation irradiation is undetected through a detection process), the power consumption state may automatically shift from the image-capturing state to the low-consumption state.

In the stand-alone mode, the control unit 22 of the radiographic image capturing apparatus 1 executes its own processing without the image capturing control by the console 58, precisely controls the operation of the functional units, such as the scan driving unit 15 and the readout circuits 17, and stores the generated image data D in the storage unit 23.

[Problems in Controlled Mode and Stand-Alone Mode]

In the controlled mode, the console 58 controls image capturing on the basis of the capturing order information, as described above, and automatically establishes the correspondence between the radiographic images generated on the basis of the captured image data D and the capturing order information. Thus, the medical worker or radiologist should merely confirm the correct correspondence established by the console 58. This enables at least ready establishment of the correct correspondence between the radiographic images and the capturing order information.

Unfortunately, the image capturing control by the console 58 on the basis of the capturing order information, as described above, leads to incorrect correspondence between the radiographic images and the capturing order information established by the console, if the operator or radiologist performs an additional image capturing not included in the capturing order information, because the order of the generated radiographic images will be shifted by one from the order of the capturing order information.

Also, if the operator or radiologist performs extra image recapturing after image capturing suspected to be unsuccessful, the order of the generated radiographic images will be shifted by one from the order of the capturing order information. This causes the same drawback as described above. Consequently, in general, additional image capturing or extra image recapturing cannot be performed in the controlled mode. Additional image capturing in the controlled mode requires troublesome operations of creating new capturing order information and making the console fetch the new capturing order information.

If the operator or radiologist cancels or invalidates the previous image capturing corresponding to one piece of capturing order information through the console 58 in the controlled mode, extra recapturing of an image will not cause the drawbacks described above. In other words, the drawbacks described above occur only when extra image recapturing is performed without cancellation of the previous image capturing through the console 58.

In contrast, the stand-alone mode is advantageous in that the operator or radiologist can freely perform image capturing without the control by the console 58 or restriction based on the capturing order information. Thus, non-scheduled additional image capturing or extra image recapturing after unsuccessful image capturing can be discretionally instructed by the operator.

Since the console 58 does not establish correspondence between the radiographic images generated on the basis of the captured image data D and the capturing order information, the medical worker or radiologist is compelled to carry out the troublesome operation of establishing the correspondence between the radiographic images and the capturing order information by himself/herself.

[Configuration Inherent in Present Invention]

The radiographic image capturing apparatus 1 according to present invention can switch the image capturing mode between the controlled mode and the stand-alone mode. Upon switch of the image capturing mode between the controlled mode and the stand-alone mode, the control unit 22 of the radiographic image capturing apparatus 1 performs its own process so as to meet the switched image capturing mode in response to the switch of the image capturing mode.

In specific, if the image capturing mode is switched to the controlled mode, the control unit 22 performs its own process under the image capturing control by the console 58. If the image capturing mode is switched to the stand-alone mode, the control unit 22 switches its own process to a stand-alone process performed without the image capturing control by the console 58.

According to such a configuration, if the operator or radiologist wants to perform an additional image capturing not included in the capturing order information while the radiographic image capturing apparatus 1 captures the image in the controlled mode, the additional image capturing can be appropriately performed by switching the image capturing mode of the radiographic image capturing apparatus 1 from the controlled mode to the stand-alone mode.

Image capturing in a fully equipped facility, such as the image capturing room R1 (see FIG. 3), is performed by switching the image capturing mode of the radiographic image capturing apparatus 1 to the controlled mode and sequentially capturing images under the control of the console 58. Alternatively, the radiographic image capturing apparatus 1 and the mobile medical cart 60 may be carried into a hospital room R3 (see FIG. 8) or the home of the patient without the console 58, to perform image capturing after switching the image capturing mode of the radiographic image capturing apparatus 1 to the stand-alone mode. In this way, the operator or radiologist can perform image capturing of a patient who has difficulties in mobility and cannot enter the image capturing room R1 while appropriately and freely changing the order of image capturing of sites of the body to be captured, depending on the situation.

Thus, the radiographic image capturing apparatus 1 is easy to use by the operator or radiologist and can certainly perform image capturing while achieving different advantages in the controlled and stand-alone image capturing modes.

[Advantageous Effects]

As described above, in the radiographic image capturing apparatus 1 and the radiographic image capturing system 50 according to this embodiment, the image capturing mode of the radiographic image capturing apparatus 1 can be switched between the controlled mode in which image capturing is performed under the control of the external console 58 and the stand-alone mode in which image capturing is autonomously performed without the control of the console 58. Upon switch of the image capturing mode between the controlled mode and the stand-alone mode, the control unit 22 performs its own process so as to meet the switched image capturing mode in response to the switch of the image capturing mode.

Thus, the radiographic image capturing apparatus 1 is easy to use by the operator or radiologist and can certainly perform image capturing while achieving different advantages in the controlled and stand-alone image capturing mode.

[Switch of Image Capturing Mode]

[Automatic Switching]

The image capturing mode of the radiographic image capturing apparatus 1 may be automatically switched by the control unit 22 of the radiographic image capturing apparatus 1. Alternatively, the operator or radiologist may manually switch the image capturing mode. For automatic switching of the image capturing mode of the radiographic image capturing apparatus 1 by the control unit 22, the control unit 22 may be configured to automatically switch to the image capturing mode suitable for a use environment of the radiographic image capturing apparatus. Examples of automatic switching by the control unit 22 of the radiographic image capturing apparatus 1 will now be described.

The default (initial) image capturing mode of the radiographic image capturing apparatus 1 can be discretionally set to the stand-alone mode or the controlled mode by the user (a worker at a facility such as a hospital, or an operator or radiologist). Alternatively, the default image capturing mode of the radiographic image capturing apparatus 1 may be set to neither the stand-alone mode nor the controlled mode.

Example 1 of Automatic Switching

For use of the radiographic image capturing apparatus 1 in the image capturing room R1, for example, image capturing by the radiographic image capturing apparatus 1 can be performed smoothly under the control of the console 58, and establishment of the correspondence between the radiographic images and the capturing order information by the console 58 is convenient for the operator or radiologist. Thus, for use of the radiographic image capturing apparatus 1 in the image capturing room R1, for example, automatic switching of the image capturing mode of the radiographic image capturing apparatus 1 from the stand-alone mode to the controlled mode is convenient for the operator.

Thus, for use of the radiographic image capturing apparatus 1 in the image capturing room R1 in the stand-alone mode, the control unit 22 of the radiographic image capturing apparatus 1 may automatically switch the image capturing mode from the stand-alone mode to the controlled mode from the stand-alone mode to the controlled mode. If the radiographic image capturing apparatus 1 is already in the controlled mode in [Example 1 of Automatic Switching], the image capturing mode remains in the controlled mode.

For use of the radiographic image capturing apparatus 1 in the image capturing room R1, the radiographic image capturing apparatus 1 is most often loaded in the cassette holder 51a of the photography platform 51 described above (see FIG. 3). Although not illustrated, the connector 27 (see FIG. 1) of the radiographic image capturing apparatus 1 is connected to another connector disposed inside the cassette holder 51a.

Figure 10:
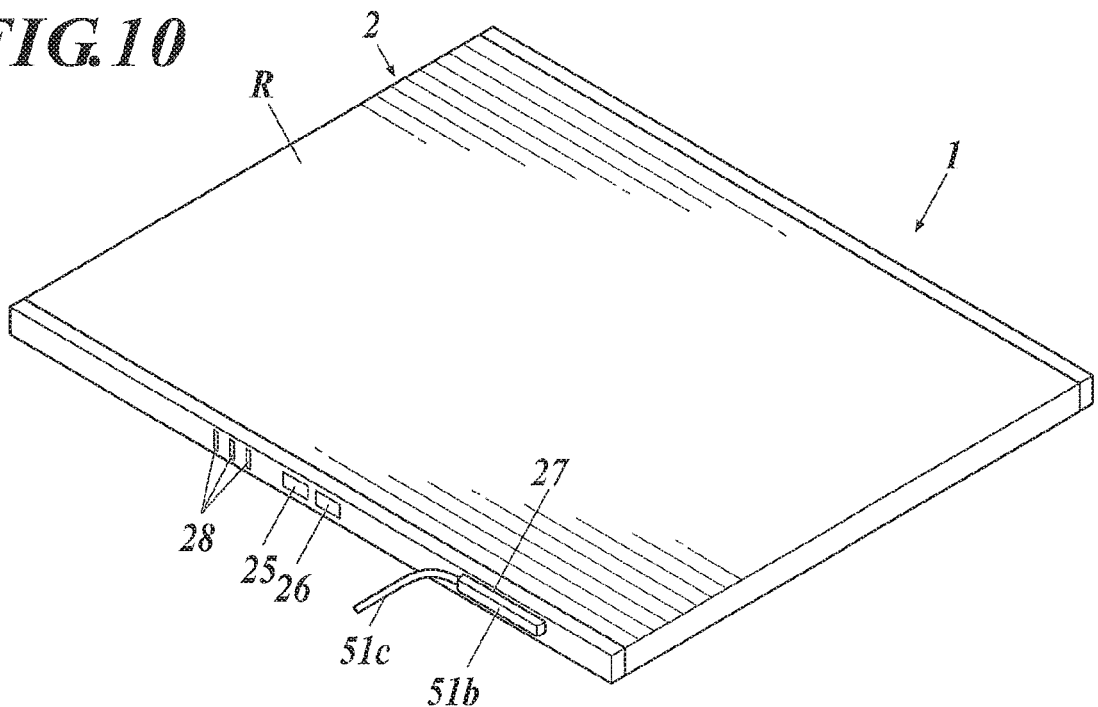
FIG. 10 illustrates a connector of the radiographic image capturing apparatus in connection with a connector at the tip of a cable.

Alternatively, for use of the radiographic image capturing apparatus 1 in the image capturing room R1, the radiographic image capturing apparatus 1 may be placed on a top board and the subject or patient may lay on the radiographic image capturing apparatus 1, instead of loading the radiographic image capturing apparatus 1 in the cassette holder 51a on the photography platform 51B for image capturing in a recumbent position. In such the case, a connector 51b at the tip of a cable 51c of the photography platform 51 is connected to the connector 27 of the radiographic image capturing apparatus 1, as illustrated in FIG. 10, for example.

Alternatively, the radiographic image capturing apparatus 1 residing in the image capturing room R1 may be inserted into the cradle 55, as illustrated in FIGS. 3 and 4. In such a case, the connector 27 of the radiographic image capturing apparatus 1 is connected to the connector 55a of the cradle 55.

For use of the radiographic image capturing apparatus 1 in the image capturing room R1, the connector 27 of the radiographic image capturing apparatus 1 is often connected to another connector, such as the connector inside the cassette holder 51a of the photography platform 51, the connector 51b of the cable 51c of the photography platform 51, or the connector 55a of the cradle 55.

The control unit 22 of the radiographic image capturing apparatus 1 preliminarily stores identification information on the devices residing in the image capturing room R1 and having connectors in a memory or a program, for example. Upon connection of the connector 27 of the radiographic image capturing apparatus 1 and another connector, the control unit 22 determines whether the identification information on the connected counterpart device sent via the other connector is included in the preliminarily stored identification information. If the control unit 22 finds the identification information on the device in the preliminarily stored identification information, the control unit 22 determines that the radiographic image capturing apparatus 1 is to be used in the image capturing room R1 and automatically switches the image capturing mode of the radiographic image capturing apparatus 1 from the stand-alone mode to the controlled mode.

In this way, the control unit 22 of the radiographic image capturing apparatus 1 can switch the image capturing mode of the radiographic image capturing apparatus 1 from the stand-alone mode to the controlled mode in response to connection of the connector 27 of the radiographic image capturing apparatus 1 and another connector residing in the image capturing room R1 (i.e., the connector inside the cassette holder 51a of the photography platform 51, the connector 51b of the cable 51c of the photography platform 51, or the connector 55a of the cradle 55).

For a photography platform 51 into which a traditional computed radiography (CR) cassette is loaded, for example, a connector is often omitted inside the cassette holder 51a of the photography platform 51. In such the case, the radiographic image capturing apparatus 1 may be loaded in the cassette holder 51a of the photography platform 51 while the connector 51b of the cable 51c of the photography platform 51 is connected to the connector 27 of the radiographic image capturing apparatus 1, to establish wired communication via the cable 51c. Alternatively, the radiographic image capturing apparatus 1 may be loaded in the cassette holder 51a of the photography platform 51 without connection of the radiographic image capturing apparatus 1 and the cable 51c and wireless communication may be established with an external unit via the antenna 29 (see FIG. 2).

The radiographic image capturing apparatus 1 placed on the top board of the photography platform 51B for image capturing in a recumbent position may also establish wireless communication with an external unit via the antenna 29 without connection of the radiographic image capturing apparatus 1 and the cable 51c.

The control unit 22 of the radiographic image capturing apparatus 1 preliminarily stores identification information, such as service set identifiers (SSIDs), for wireless communication with the access point 53 (see FIG. 3) residing in the image capturing room R1, in a memory or a program, for example. Upon establishment of wireless communication between the antenna 29 of the radiographic image capturing apparatus 1 and the access point 53, the control unit 22 determines whether the preliminarily stored identification information includes the identification information or SSID sent from the access point 53. If the preliminarily stored identification information includes the identification information or SSID sent from the access point 53, the control unit 22 determines that the radiographic image capturing apparatus 1 is to be used in the image capturing room R1 and automatically switches the image capturing mode of the radiographic image capturing apparatus 1 from the stand-alone mode to the controlled mode.

Upon establishment of wireless communication between the antenna 29 of the radiographic image capturing apparatus 1 and the access point 53 residing in the image capturing room R1, the control unit 22 of the radiographic image capturing apparatus 1 may switch the image capturing mode of the radiographic image capturing apparatus 1 from the stand-alone mode to the controlled mode. If multiple access points 53 reside in the image capturing room R1, the control unit 22 of the radiographic image capturing apparatus 1 preliminarily stores identification information on all the access points 53 in the image capturing room R1. Upon establishment of wireless communication with any one of these access points 53, the control unit 22 may switch the image capturing mode from the stand-alone mode to the controlled mode.

The image capturing mode is switched in response to connection between a connector of the photography platform 51, the cable 51c, or the cradle 55 residing in the image capturing room R1 and the connector 27 of the radiographic image capturing apparatus 1 or establishment of wireless communication between the access point 53 residing in the image capturing room R1 and the antenna 29 of the radiographic image capturing apparatus 1, as described above. This automatically and certainly switches the image capturing mode of the radiographic image capturing apparatus 1 from the default stand-alone mode to the controlled mode for use of the radiographic image capturing apparatus 1 in the image capturing room R1, for example.

Thus, the image capturing mode of the radiographic image capturing apparatus 1 automatically switches to the controlled mode when the radiographic image capturing apparatus 1 is carried in the image capturing room R1 and connected to another connector, without switching by the operator or radiologist. Accordingly, the operator or radiologist can perform image capturing through familiar procedures of operations and/or processes in the controlled mode traditionally performed in the image capturing room R1. Thus, the radiographic image capturing apparatus 1 is easy to use by the operator or radiologist.

In such a case, image capturing can be performed smoothly under the control of the console 58, and the console 58 establishes correspondence between the radiographic images and the capturing order information. Thus, the workload of the operator or radiologist can be reduced.

Upon disconnection of the connector 27 of the radiographic image capturing apparatus 1 and the connector of the photography platform 51 or the cable 51c, the control unit 22 of the radiographic image capturing apparatus 1 may switch back the image capturing mode of the radiographic image capturing apparatus 1 to the default image capturing mode, if the default image capturing mode is established. In detail, if the default image capturing mode of the radiographic image capturing apparatus 1 is set to the stand-alone mode, the image capturing mode of the radiographic image capturing apparatus 1 switches from the controlled mode to the stand-alone mode, whereas if the default image capturing mode is the controlled mode, the image capturing mode of the radiographic image capturing apparatus 1 remains the controlled mode.

If the radiographic image capturing apparatus 1 in the stand-alone mode as a default image capturing mode is placed in the cradle 55 instead of being connected to a connector in the image capturing room R1, the processes described above are not applicable. If the image capturing mode of the radiographic image capturing apparatus 1 switches back from the controlled mode to the default stand-alone mode when the radiographic image capturing apparatus 1 is draw out from the cradle 55 and the connection between the connector 27 of the radiographic image capturing apparatus 1 and the connector 55a of the cradle 55, which has been established when the radiographic image capturing apparatus 1 has been placed in the cradle 55, is released, there is no point in switching the image capturing mode of the radiographic image capturing apparatus 1 from the default stand-alone mode to the controlled mode by the control unit 22 of the radiographic image capturing apparatus 1, which has determined that the radiographic image capturing apparatus 1 is to be used in the image capturing room R1, in response to the placement of the radiographic image capturing apparatus 1 in the cradle 55 (i.e., connection of the connector 27 of the radiographic image capturing apparatus 1 and the connector 55a of the cradle 55).

Concretely, the image capturing mode of the radiographic image capturing apparatus 1 in the default stand-alone mode switches to the controlled mode in response to connection of the radiographic image capturing apparatus 1 and the cradle 55 via their connectors due to placement of the radiographic image capturing apparatus 1 in the cradle 55. If the image capturing mode of the radiographic image capturing apparatus 1 switches back to the default stand-alone mode in response to removal of the radiographic image capturing apparatus 1 from the cradle 55, the image capturing mode of the radiographic image capturing apparatus 1 remains in the controlled mode only while the radiographic image capturing apparatus 1 is placed in the cradle 55. There is no point in switching back the image capturing mode of the radiographic image capturing apparatus 1 to the stand-alone mode upon removal of the radiographic image capturing apparatus 1 from the cradle 55, the radiographic image capturing apparatus 1 being to be used for image capturing in the image capturing room R1.

In a case where the default image capturing mode of the radiographic image capturing apparatus 1 is set to the stand-alone mode and the radiographic image capturing apparatus 1 is configured such that the default stand-alone mode switches to the controlled mode in response to placement of the radiographic image capturing apparatus 1 in the cradle 55, the radiographic image capturing apparatus 1 is configured such that the image capturing mode thereof remains the controlled mode even if the radiographic image capturing apparatus 1 is removed from the cradle 55 and the connectors are disconnected.

In this case, the radiographic image capturing apparatus 1 may be configured such that the image capturing mode thereof may switch from the controlled mode to the default stand-alone mode, for example, when the radiographic image capturing apparatus 1 is placed in the cradle 55 again before being carried out of the image capturing room R1, or when the radiographic image capturing apparatus 1 is placed in a cradle 55 disposed in a storage cabinet (not shown).

In a case of multiple image capturing rooms, if the radiographic image capturing apparatus 1, which has been placed in a first cradle 55 in a first image capturing room and switched to the controlled mode, is placed in a second cradle 55 in a second image capturing room while in the controlled mode, the control unit 22 of the radiographic image capturing apparatus 1 can identify the counterpart device, whose connector is connected to the connector 27 of the radiographic image capturing apparatus 1, as the second cradle 55 based on the identification information of the counterpart device, as described above, and determine that the radiographic image capturing apparatus 1 is to be used for image capturing in the second image capturing room. Thus, the control unit 22 can keep the controlled mode without switching back to the stand-alone mode.

Example 2-1 of Automatic Switching

In a case where the radiographic image capturing apparatus 1 is removed from a facility and carried into the home of a patient for use, for example, it is often convenient for the operator or radiologist to perform image capturing of the subject or patient while appropriately and freely changing the capturing order of capturing sites of the subject or patient, depending on the situation, as described above. In a case where the radiographic image capturing apparatus 1 is used outside a facility such as a hospital, the control unit 22 of the radiographic image capturing apparatus 1 may automatically switch the image capturing mode of the radiographic image capturing apparatus 1 from the controlled mode to the stand-alone mode. If the radiographic image capturing apparatus 1 is already in the stand-alone mode in [Example 2-1 of Automatic Switching] and [Example 2-2 of Automatic Switching] to be described later, the image capturing mode remains in the stand-alone mode.

Although not illustrated, a position measuring unit, such as a global positioning system (GPS), is provided in the radiographic image capturing apparatus 1, and the control unit 22 of the radiographic image capturing apparatus 1 preliminarily stores information on the latitude and longitude of the facility such as a hospital in a memory or program, for example. The control unit 22 may switch the image capturing mode of the radiographic image capturing apparatus 1 from the controlled mode to the stand-alone mode when the control unit 22 determines that the radiographic image capturing apparatus 1 resides outside the facility such as a hospital based on the position of the radiographic image capturing apparatus 1 measured by the position measuring unit.

In place of using a GPS, the position measuring unit may be configured to measure the distance and direction of movement of the radiographic image capturing apparatus 1, for example, and the control unit 22 of the radiographic image capturing apparatus 1 may preliminarily store, in a memory or a program, information on the shape of the facility such as a hospital in the case where the storage cabinet accommodating the radiographic image capturing apparatus 1 in the facility such as a hospital is the center in every direction. The control unit 22 may determine whether the radiographic image capturing apparatus 1 resides inside or outside the facility such as a hospital on the basis of the distance and direction of movement of the radiographic image capturing apparatus 1 measured by the position measuring unit. Alternatively, any other method or unit may be used to measure the position of the radiographic image capturing apparatus 1.

In case where a GPS is used as the measuring unit, the GPS may not be able to measure the position of the radiographic image capturing apparatus 1 residing inside a hospital building or the home of a patient. In such a case, the radiographic image capturing apparatus 1 may determine the position of the radiographic image capturing apparatus 1 to be outside the facility if the last position of the radiographic image capturing apparatus 1 measured by the GPS is far away from the facility such as a hospital, whereas the radiographic image capturing apparatus 1 may determine the position of the radiographic image capturing apparatus 1 to be inside the facility if the last position of the radiographic image capturing apparatus 1 measured by the GPS is inside or close to the facility such as a hospital.

Example 2-2 of Automatic Switching

In a large-scale facility such as a hospital, the image capturing room R1 (see FIG. 3) and the hospital room R3 (see FIG. 8) may be on different floors, e.g., the image capturing room R1 in a lower floor or the basement and the hospital room R3 in a higher floor. In a case where the radiographic image capturing apparatus 1 is carried in the hospital room R3 and used in round on patients, it is often convenient for the operator or radiologist to perform image capturing of a subject or patient who has difficulties in mobility and cannot enter the image capturing room R1 while appropriately and freely changing the capturing order of capturing sites of the subject or patient, depending on the situation, as described above.

Thus, the control unit 22 of the radiographic image capturing apparatus 1 may automatically switch the image capturing mode of the radiographic image capturing apparatus 1 from the controlled mode to the stand-alone mode if the radiographic image capturing apparatus 1 is used in round on patients in the hospital room R3.

Although not illustrated, an altitude measuring unit such as an altimeter for measuring the height or altitude of the radiographic image capturing apparatus 1 may be provided in the radiographic image capturing apparatus 1, and the control unit 22 of the radiographic image capturing apparatus 1 may preliminarily store, in a memory or a program, information on the altitude of the floor on which the image capturing room R1 resides and information on the altitude of the floor on which the hospital room R3 resides in the facility such as a hospital.

The control unit 22 may switch the image capturing mode of the radiographic image capturing apparatus 1 from the controlled mode to the stand-alone mode if the control unit 22 determines that the radiographic image capturing apparatus 1 resides in the hospital room R3 and is used in round on patients in the hospital room R3 on the basis of the altitude of the radiographic image capturing apparatus 1 measured by the altitude measuring unit.

The control unit 22 may switch the image capturing mode of the radiographic image capturing apparatus 1 from the stand-alone mode to the controlled mode if the control unit 22 determines that the radiographic image capturing apparatus 1 resides on the floor on which the image capturing room R1 resides on the basis of the altitude of the radiographic image capturing apparatus 1 measured by the altitude measuring unit.

Example 3 of Automatic Switching

Other than the radiographic image capturing apparatus 1 residing in the image capturing room R1, the radiographic image capturing apparatus 1 may reside in the hospital room R3 and be used in round on patients in the hospital room R3 while a mobile medical cart 60 provided with a portable console 58 is also carried into the hospital room R3 for image capturing as illustrated in FIG. 8, for example. In such a case, it is convenient for the operator or radiologist to keep the image capturing mode of the radiographic image capturing apparatus 1 in the controlled mode not only in the image capturing room R1 and but also in the hospital room R3.

In a case where the radiographic image capturing apparatus 1 is used in round on patients in the hospital room R3, the cable extending from the mobile medical cart 60 (see FIG. 8) for connection with the connector 27 of the radiographic image capturing apparatus 1, as illustrated in FIG. 10, may be an obstacle for image capturing causing the operator or radiologist to trip. Thus, the radiographic image capturing apparatus 1 and the console 58 in the mobile medical cart 60 may establish wireless communication when the radiographic image capturing apparatus 1 is used in round on patients in the hospital room R3.

The hospital room R3 more often experiences deterioration of radio wave environment than the image capturing room R1 due to interference from the various electronic devices placed in the hospital room R3. The deterioration of the radio wave environment might preclude wireless communication of the control unit 22 of the radiographic image capturing apparatus 1 and the console 58 via the antenna 29 (see FIG. 2).

The control unit 22 of the radiographic image capturing apparatus 1 may automatically switch the image capturing mode of the radiographic image capturing apparatus 1 from the controlled mode to the stand-alone mode when the control unit 22 determinates that radio wave environment for wireless communication with the console 58 via the antenna 29 is deteriorated on the basis of information on the radio wave intensity measured by the communication device 30 (see FIG. 2). Also in this case, if the image capturing mode of the radiographic image capturing apparatus 1 is already the stand-alone mode, the image capturing mode remains the stand-alone mode.

The radiographic image capturing apparatus 1 can perform image capturing without wireless communication with the console 58 in this configuration. Thus, the radiographic image capturing apparatus 1 can certainly perform image capturing in the hospital room R3 even under a deteriorated radio wave environment unsuitable for wireless communication.

If the operator or radiologist does not notice the switch of the image capturing mode of the radiographic image capturing apparatus 1 to the stand-alone mode, the operator or radiologist may forget to establish the correspondence between the capturing order information and the radiographic images generated on the basis of the image data D acquired through image capturing. Thus, if the image capturing mode of the radiographic image capturing apparatus 1 is the controlled mode, it is preferred that when the image capturing mode is switched from the controlled mode to the stand-alone mode, the control unit 22 of the radiographic image capturing apparatus 1 notify the operator the switch of the image capturing mode of the radiographic image capturing apparatus 1 from the controlled mode to the stand-alone mode, as described above.

This can be achieved through illumination of an indicator 28 (see FIG. 1) of the radiographic image capturing apparatus 1 in a predetermined color or a predetermined flashing pattern or a sound generated by a sounding unit (not shown) provided in the radiographic image capturing apparatus 1, for example. Alternatively, a signal may be sent from the radiographic image capturing apparatus 1 to the portable information terminal 70 (see FIG. 8) or the console 58, to display a message on the display unit 71 of the portable information terminal 70 or the display unit 58a of the console 58, or generate a sound for notification.

In the case of deteriorated radio wave environment as described above, an operator may prefer to wait for an improvement in the radio wave environment rather than switching the image capturing mode of the radiographic image capturing apparatus 1 to the stand-alone mode and later carrying out the troublesome process of establishment of the correspondence of the radiographic images and the capturing order information. In such a case, it is inconvenient for the operator to automatically switch the image capturing mode of the radiographic image capturing apparatus 1 to the stand-alone mode in the deteriorated radio wave environment.

The control unit 22 of the radiographic image capturing apparatus 1 may send a notification of the switch of the image capturing mode of the radiographic image capturing apparatus 1 from the controlled mode to the stand-alone mode before actually switching the image capturing mode when the control unit 22 determines that radio wave environment for wireless communication with the console 58 via the antenna 29 is deteriorated. The image capturing mode of the radiographic image capturing apparatus 1 may actually switch from the controlled mode to the stand-alone mode only if the operator or radiologist performs an input operation to give permission for the switch by operating the radiographic image capturing apparatus 1, the portable information terminal 70, or the console 58.

According to such a configuration, if the operator does not mind the later process of establishment of the correspondence between the radiographic images and the capturing order information and prefers the early completion of image capturing, the operator may perform the input operation to give permission to switch the image capturing mode of the radiographic image capturing apparatus 1 from the controlled mode to the stand-alone mode. Alternatively, if the operator prefers waiting an improvement in the radio wave environment to performing the process of establishment of the correspondence between the radiographic images and the capturing order information later, the operator may wait for an improvement in the radio wave environment in the controlled mode of the radiographic image capturing apparatus 1 without the input operation to give permission (or with an input operation of rejection), and resume the image capturing after improvement of the radio wave environment.

This allows the image capturing mode of the radiographic image capturing apparatus 1 to be switched to the stand-alone mode or remain the controlled mode depending on the intension of the operator. Thus, the radiographic image capturing apparatus 1 is easy to use by the operator or radiologist. Alternatively, before performing the series of image capturing operations, the operator or radiologist may preliminarily determine whether to switch the image capturing mode of the radiographic image capturing apparatus 1 from the controlled mode to the stand-alone mode in case of a deteriorated radio wave environment and input the determined result through the console 58 or the portable information terminal 70, or directly input the result to the radiographic image capturing apparatus 1, for example.

Alternatively, if the control unit 22 of the radiographic image capturing apparatus 1 detects an improvement in the radio wave environment after the image capturing mode of the radiographic image capturing apparatus 1 switches from the controlled mode to the stand-alone mode due to a deteriorated radio wave environment for wireless communication with the console 58 via the antenna 29, the image capturing mode of the radiographic image capturing apparatus 1 may switch back to the default image capturing mode. In specific, if the default image capturing mode of the radiographic image capturing apparatus 1 is set to the controlled mode, the image capturing mode switches from the stand-alone mode to the controlled mode, whereas if the default image capturing mode is set to the stand-alone mode, the image capturing mode remains the stand-alone mode.

In this case also, the radiographic image capturing apparatus 1 may be configured as described below. Specifically, if the default image capturing mode of the radiographic image capturing apparatus 1 is set to the controlled mode, the control unit 22 of the radiographic image capturing apparatus 1 sends a notification about the switch of the image capturing mode of the radiographic image capturing apparatus 1 from the stand-alone mode to the controlled mode before switching the image capturing mode of the radiographic image capturing apparatus 1 to the default controlled mode, as described above. If the operator performs the input operation to give permission for the switch, the control unit 22 switches back the image capturing mode of the radiographic image capturing apparatus 1 from the stand-alone mode to the default controlled mode. Image capturing can be performed in accordance with the intention of the operator in such a configuration, and thus, the radiographic image capturing apparatus 1 is easy to use by the operator or radiologist.

Example 4 of Automatic Switching

The radiographic image capturing apparatus 1 generates the image data D after radiation is irradiated, as illustrated in FIG. 6, for example, transfers data on preview images to the console 58, and repeats the voltage application sequence illustrated in FIG. 6 without radiation irradiation to read the offset data O, as illustrated in FIG. 7. The radiographic image capturing apparatus 1 then transfers the image data D and the offset data O to the console 58. Alternatively, the radiographic image capturing apparatus 1 may carry out processing such as calculation of the true image data D* by subtracting the offset data O from the image data D for every radiation detecting element 7 and then transfer the processed data to the console 58.

During this process of reading of the offset data O or transfer of the image data D and the offset data O to the console 58 after generation of the image data D at the radiographic image capturing apparatus 1, the operator or radiologist may operate the exposure switch 56 of the radiation irradiating apparatus 57 (see FIGS. 3 and 8) to execute a next image capturing, i.e., may cause radiation irradiation for a subsequent image capturing.

In a traditional controlled mode, after the resetting of the radiation detecting elements 7, which carried out after completion of the reading of the offset data O and the transfer of the image data D and the offset data O to the console 58, an interlock release signal is sent from the radiographic image capturing apparatus 1 to the radiation irradiating apparatus 57, to start radiation irradiation. The operator or radiologist has to wait for the radiation irradiation during this time and thus, cannot perform image capturing at a desired timing.

If such a wait is inevitable or possible, the control unit 22 of the radiographic image capturing apparatus 1 may automatically switch the image capturing mode of the radiographic image capturing apparatus 1 from the controlled mode to the stand-alone mode.

In specific, if the operator or radiologist operates the exposure switch 56 of the radiation irradiating apparatus 57 to send a radiation start signal from the radiation irradiating apparatus 57 during reading of the offset data O or transfer of the image data D or the offset data O to the console 58, for example, the control unit 22 of the radiographic image capturing apparatus 1 may automatically switch the image capturing mode of the radiographic image capturing apparatus 1 from the controlled mode to the stand-alone mode.

Simultaneous to the switch of the image capturing mode, the control unit 22 of the radiographic image capturing apparatus 1 halts the reading of the offset data O and the transfer of the image data D and the offset data O to the console 58 executed at that time, and stores the image data D and/or the offset data O in the storage unit 23 (see FIG. 2) (stand-alone mode). Immediately after the resetting of the radiation detecting elements 7, the control unit 22 may send an interlock release signal to the radiation irradiating apparatus 57.

If capturing order information is to be sent to the radiographic image capturing apparatus 1 before image capturing, and when the control unit 22 of the radiographic image capturing apparatus 1 determines that multiple consecutive images are to be captured for a single patient on the basis of the received capturing order information, the control unit 22 may automatically switch the image capturing mode of the radiographic image capturing apparatus 1 from the controlled mode to the stand-alone mode before or at the start of image capturing.

Also in this case, the control unit 22 of the radiographic image capturing apparatus 1 may store the image data D, the offset data O and other data in the storage unit 23, and transfer the image data D and other data to the console 58 later, namely, at the time when wireless or wired communication with the console 58 is established.

In either case described above, the reading of the offset data O may be performed once or more in response to completion of the series of image capturing operations (or before the start of the series of image capturing operations in the latter case). Also in either case, the control unit 22 of the radiographic image capturing apparatus 1 may send a notification about the switch of the image capturing mode of the radiographic image capturing apparatus 1 to the stand-alone mode to the operator or radiologist, and/or switch the image capturing mode to the stand-alone mode when the operator performs the input operation to give permission for the switch.

[Manual Switching]

In the examples described above, the control unit 22 of the radiographic image capturing apparatus 1 automatically switches the image capturing mode of the radiographic image capturing apparatus 1. Alternatively, the operator or radiologist may manually switch the image capturing mode. Examples of manual switching will now be described.

The image capturing mode of the radiographic image capturing apparatus 1 may switch between the controlled mode and the stand-alone mode in response to a predetermined operation to the switch, such as long-push of the selection switch 26 (see FIG. 1) or simultaneous pushing of the selection switch 26 and the power switch 25 (or any other button not illustrated).

Although not illustrated, the radiographic image capturing apparatus 1 may be provided with a vibration detector, such as vibration sensor or acceleration sensor. The control unit 22 of the radiographic image capturing apparatus 1 can detect, with the vibration detector, a predetermined vibration applied to the radiographic image capturing apparatus 1 by the operator or radiologist tapping the casing 2 of the radiographic image capturing apparatus 1 in a predetermined pattern and, in response, may switch the image capturing mode of the radiographic image capturing apparatus 1 between the controlled mode and the stand-alone mode.

Alternatively, a sound detector, such as a microphone, may be provided in the casing 2 of the radiographic image capturing apparatus 1. The control unit 22 of the radiographic image capturing apparatus 1 can detect, with the sound detector, a predetermined word or sound uttered by the operator or radiologist, and, in response, may switch the image capturing mode of the radiographic image capturing apparatus 1 between the controlled mode and the stand-alone mode.

Alternatively, the portable information terminal 70 carried by the operator E or radiologist, as illustrated in FIG. 8, may be operated to transmit a predetermined signal from the portable information terminal 70 to the radiographic image capturing apparatus 1, and the control unit 22 of the radiographic image capturing apparatus 1 may switch the image capturing mode of the radiographic image capturing apparatus 1 between the controlled mode and the stand-alone mode on the basis of the received signal.

Alternatively, the operator or radiologist may manually switch the image capturing mode of the radiographic image capturing apparatus 1 through any process other than those described above.

The image capturing mode of the radiographic image capturing apparatus 1 can be manually switched by the operator or radiologist, as described above. According to this configuration, if an additional image capturing not included in capturing order information is performed during image capturing in the controlled mode, the operator or radiologist can manually switch the image capturing mode of the radiographic image capturing apparatus 1 to the stand-alone mode, to perform the additional image capturing and store the image data D in the storage unit 23. The image capturing mode of the radiographic image capturing apparatus 1 can then be manually switched back to the controlled mode to resume the image capturing in the controlled mode.

From the viewpoint of the manufacturer, if the above-described radiographic image capturing apparatus 1 is to be newly introduced to a facility such as a hospital that has been using a traditional CR cassette for image capturing, the operator or radiologist may be comfortable with the image capturing process with the traditional CR cassette but uncomfortable with the image capturing process with the radiographic image capturing apparatus 1 in the controlled mode under the control of the console 58.

In such a case, image capturing can be performed in the same way as that with the traditional CR cassette if the image capturing mode of the radiographic image capturing apparatus 1 switches to the stand-alone mode. Thus, the image capturing mode of the radiographic image capturing apparatus 1 may be set to the stand-alone mode before introduction of the radiographic image capturing apparatus 1. The operator or radiologist may gradually increase the frequency of image capturing after switch of the image capturing mode to the controlled mode and gain experience in image capturing in the controlled mode.

This is also the same for a case where the radiographic image capturing apparatus 1 is exported to an emerging country. The image capturing mode of the radiographic image capturing apparatus 1 is switched to the stand-alone mode before export. The exported radiographic image capturing apparatus 1 should be used in the stand-alone mode until a service person properly installs the radiographic image capturing apparatus 1. After the service person explains to the operator how to use the radiographic image capturing apparatus 1 under the control of the console 58, i.e., how to use the radiographic image capturing apparatus 1 and the console 58 in the controlled mode, the image capturing mode of the radiographic image capturing apparatus 1 may be switched between the controlled mode and the stand-alone mode.

If the console 58 is not installed in the facility in the emerging country, the image data D captured by the radiographic image capturing apparatus 1 in the stand-alone mode may be transferred to a service station in Japan via the Internet so as to generate radiographic images in Japan, and the radiographic images may be sent back to the facility in the emerging country. The image data D to be transferred is preferably encrypted or protected with a public key, for example. Alternatively, the image data D and the radiographic images may be transferred after adding noise (watermark) removeable through predetermined processing.

[Configurational Example of Processing in Stand-Alone Mode]

Configuration examples of processing by the radiographic image capturing apparatus 1 and the console 58 in the stand-alone mode of the radiographic image capturing apparatus 1 will now be described.

Image capturing in only the stand-alone mode will be described for simplification. It is needless to say that the image capturing mode can switch also to the controlled mode. In the image capturing described below, the radiographic image capturing apparatus 1 detects the start of radiation irradiation by itself, without communication of signals between the radiographic image capturing apparatus and the radiation irradiating apparatus 57. If the radiographic image capturing apparatus 1 and the radiation irradiating apparatus 57 are to communicate signals, a process of determining whether the radiographic image capturing apparatus 1 has received a radiation start signal from the radiation irradiating apparatus 57 is performed in place of the process of determining whether the start of radiation irradiation is detected (Step S2).

Configurational Example A

Figure 11:
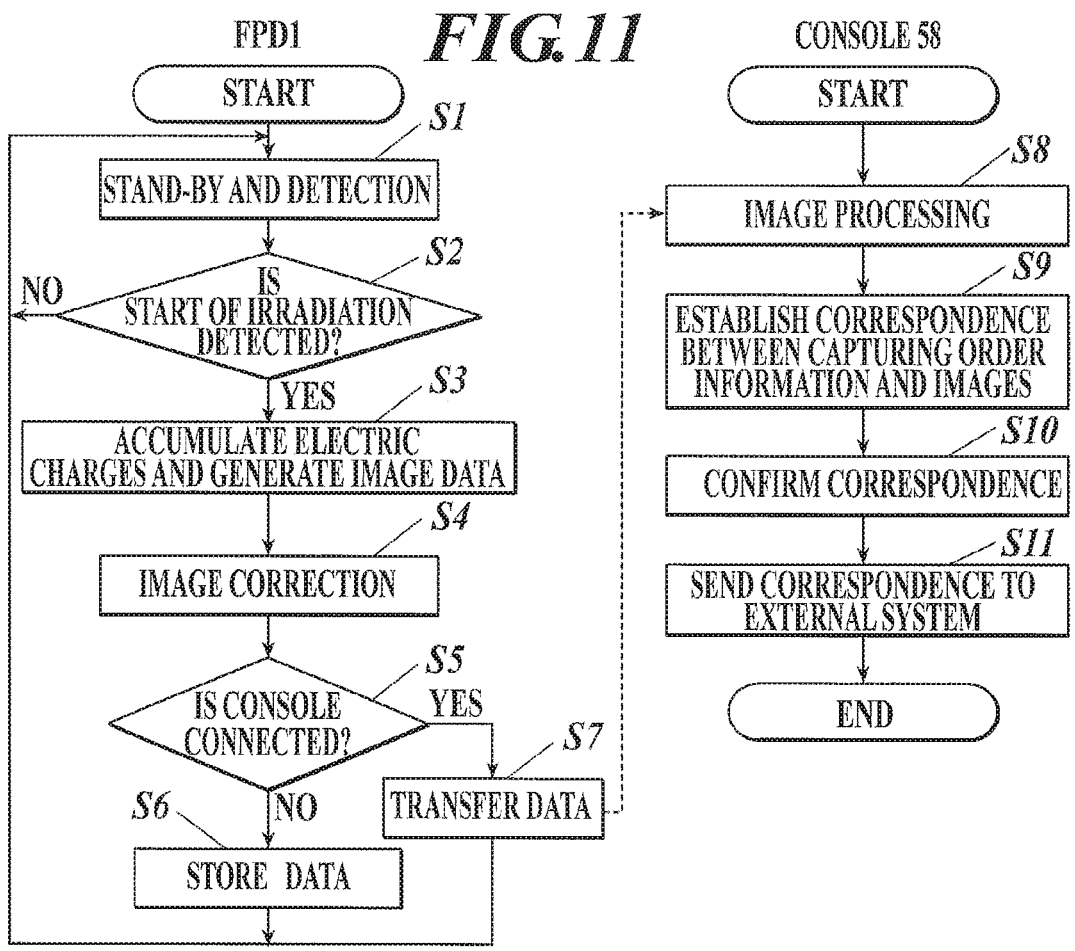
FIG. 11 is a flow chart illustrating the processes carried out in a configurational example A while the image capturing mode of the radiographic image capturing apparatus is a stand-alone mode.

With reference to the flow chart in FIG. 11, the control unit 22 of the radiographic image capturing apparatus 1 (FPD 1 in FIG. 11) performs a detecting process to detect the start of radiation irradiation in a stand-by mode after the functional units of the radiographic image capturing apparatus 1 complete the pre-processing for image capturing (Step S1). The start of radiation irradiation can be detected by the radiographic image capturing apparatus 1 through methods disclosed in the domestic and international publications mentioned above, for example.

Upon detection of the start of radiation irradiation from the radiation source 52 of the radiation irradiating apparatus 57 (see FIGS. 3 and 8) (YES in Step S2), the control unit 22 causes the gate driver 15b of the scan driving unit 15 (see FIG. 2) to apply OFF voltages to the scanning lines 5 to turn off the TFTs 8 to shift to a charge accumulating state, and to sequentially apply ON voltages to the scanning lines 5 to generate image data D (Step S3).

If offset data O is to be read after image capturing, the control unit 22 subsequently repeats the same sequence without radiation irradiation to read the offset data O. Alternatively, the offset data O may be read before image capturing and stored in the storage unit 23, so that the stored offset data O can be used in the image correction described below.

The control unit 22 then performs image correction (Step S4). Alternatively, the image correction may be performed by the console 58, in place of the radiographic image capturing apparatus 1. In such the case, the image data D as raw data, the offset data O and other data are transferred from the radiographic image capturing apparatus 1 to the console 58 (Step S7). In the stand-alone mode, data is often stored in the storage unit 23 of the radiographic image capturing apparatus 1. Thus, image correction (Step S4) may be performed by the radiographic image capturing apparatus 1 to reduce the volume of stored data.

In image correction, the control unit 22 calculates the true image data D* from the image data D and the offset data O as described above, and carries out image correction, such as gain correction, defect correction (including correction of point defects and line defects) and gradation processing, on the true image data D*, to generate a radiographic image p. Other appropriate image correction processes may also be carried out, such as correction of unevenness of the image due to unevenness in the sensitivity of the scintillator (not shown).

If the radiographic image capturing apparatus 1 has not established wired or wireless communication with the console 58 (NO in Step S5), the control unit 22 stores the data on the corrected radiographic image p in the storage unit 23 (Step S6) as described above, and prepares for the next image capturing (Step S1). In the stand-alone mode, the data on the corrected radiographic images p (or image data D and offset data O, if image correction is omitted, the same hereinafter) are thus stored in the storage unit 23 until the radiographic image capturing apparatus 1 is connected to the console 58.

If the radiographic image capturing apparatus 1 establishes wired or wireless communication with the console 58 (YES in Step s5), the control unit 22 transfers the data on the radiographic images p to the console 58 (Step S7). If the data on the already-captured radiographic images p are stored in the storage unit 23 at that time, the data on the radiographic images p are transferred to the console 58 (Step S7) in response to establishment of wired or wireless connection of the radiographic image capturing apparatus 1 to the console 58 (YES in Step S5).

If image capturing is performed while wired or wireless connection is established between the radiographic image capturing apparatus 1 and the console 58 (YES in Step S5), the data on the radiographic image p is transferred from the radiographic image capturing apparatus 1 to the console 58 after every image capturing, even if the image capturing mode of the radiographic image capturing apparatus 1 is the stand-alone mode.

In either case, the console 58 does not establish the correspondence between the capturing order information and the radiographic images p in the stand-alone mode, unlike in the controlled mode. Thus, the medical worker or radiologist should establish the correspondence (also referred to as pro-registration) between the capturing order information and the radiographic images p with the console 58.

In detail, upon reception of the data on the radiographic images p transferred from the radiographic image capturing apparatus 1 (Step S7), the console 58 carries out image processing on the radiographic images p (Step S8). The console 58 carries out complicated image processing involving removal of periodic noise components superposed on a radiographic image p, such as moire stripes in the radiographic image p captured with a grid (not shown), through calculations such as Fourier transform, unlike the image correction described above.

In this configurational example A, such complicated image processing is carried out by the console 58 because if the radiographic image capturing apparatus 1 carries out this processing, the battery 24 (see FIG. 2) will be consumed. Alternatively, the processing may be carried out by the radiographic image capturing apparatus 1. Alternatively, image correction and image processing may be carried out by the console 58, as described above.

The process up to image processing (Step S8) is automatically carried out by the console 58, whereas the establishment of the correspondence between the capturing order information and the radiographic images p (Step S9) is carried out by a medical worker or radiologist, as described above. If the data on the radiographic images p is transferred from the radiographic image capturing apparatus 1 after each image capturing, the correspondence between the capturing order information and the radiographic images p may be established after each image capturing or after the entire series of image capturing operations.

A configurational example for correct and ready establishment of the correspondence between the capturing order information and the radiographic images p will be described below. The medical worker receives the required capturing order information from the HIS or RIS prior to or at this point. If not prepared, the capturing order information should be prepared and input to the console 58.

When the medical worker or radiologist ends the establishment of the correspondence between the capturing order information and the radiographic images p (Step S9) and confirms the correspondence (Step S10), the console 58 sends the capturing order information and the connected radiographic images p correlated to each other to an external system, such as the PACS described above (Step S11). The process then ends.

Configurational Example B

For image capturing by the radiographic image capturing apparatus 1 in the stand-alone mode, the radiographic image capturing apparatus 1 may carry out all processes, without processing by the console 58.

Figure 12:
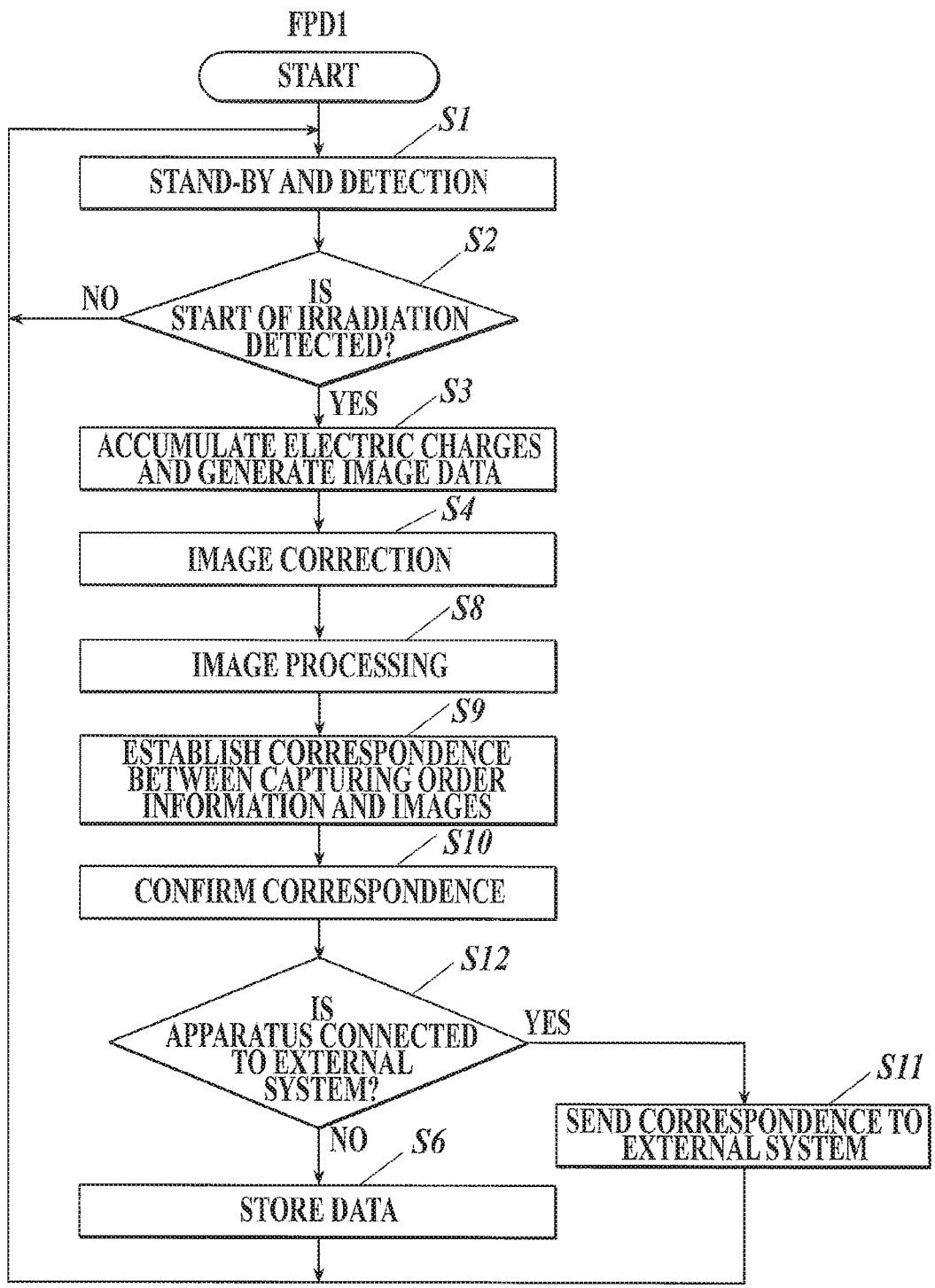
FIG. 12 is a flow chart illustrating the processes carried out in a configurational example B while the image capturing mode of the radiographic image capturing apparatus is a stand-alone mode.

With reference to the flow chart in FIG. 12, the image processing (Step S8), the establishment of the correspondence between the capturing order information and the radiographic images p (Step S9), and the confirmation process (Step S10), which are carried out by the console 58 in the configurational example A, are carried by the radiographic image capturing apparatus 1 (FPD 1 in FIG. 12).

The flow chart in FIG. 12 illustrates the case where the confirmation process (Step S10) is carried out after each image capturing. Alternatively, the control unit 22 of the radiographic image capturing apparatus 1 automatically establishes the correspondence between the capturing order information items and the radiographic images p (Step S9) after every image capturing operation, and then the medical worker or radiologist may confirm (Step S10) the correspondence after the series of image capturing operations.

If the radiographic image capturing apparatus 1 includes a display unit as in the radiographic image capturing apparatus disclosed in PTL 2, the correspondence between the capturing order information and the radiographic images p can be established while the capturing order information and the radiographic images p are displayed on the display unit. Alternatively, if the radiographic image capturing apparatus 1 does not include a display unit, necessary data including the radiographic images p and the capturing order information are sent from the radiographic image capturing apparatus 1 to the portable information terminal 70 (see FIG. 8) and displayed on the display unit 71 of the portable information terminal 70, such that the operator can perform the correlation processing while viewing the portable information terminal 70.

The process illustrated in the flow chart of FIG. 12 is carried out on the prerequisite that the control unit 22 of the radiographic image capturing apparatus 1 preliminarily retrieves the necessary capturing order information from the HIS or RIS and the image capturing is carried out in accordance with the order of the capturing order information. Image capturing in the stand-alone mode is characteristic in that the operator or radiologist can freely modify the order of image capturing of a site of the body to be captured depending on the situation, as described above.

Thus, the image capturing often do not follow the order of the capturing order information. Consequently, the correspondence between the capturing order information and the radiographic images p automatically established by the control unit 22 of the radiographic image capturing apparatus 1 is probably inappropriate. Thus, the control unit 22 of the radiographic image capturing apparatus 1 may carry out not only the confirmation process (Step S10) but also the establishment of the correspondence between the capturing order information and the radiographic images p (Step S9) after the series of image capturing operations.

Image processing (Step S8) may require time for complicated calculation, such as Fourier transform. To avoid a long waiting time between the completion of the image processing and the next image capturing, the image processing (Step S8) may also be carried out after the series of image capturing operations.

In this configurational example B, if the radiographic image capturing apparatus 1 does not establish wired or wireless connection with an external system, such as a PACS, (NO in Step S12), the control unit 22 of the radiographic image capturing apparatus 1 stores the capturing order information and the radiographic images p having the confirmed correspondence in the storage unit 23 (Step S6). If the radiographic image capturing apparatus 1 establishes wired or wireless communication with an external system, such as a PACS, (YES in Step S12), the capturing order information and the radiographic images p having the confirmed correspondence are directly sent to the external system (Step S11) without the console 58.

The configurational examples A and B enable certain image capturing, certain generation of radiographic images p, and establishment of correct correspondence between the capturing order information and the radiographic images p during the image capturing by the radiographic image capturing apparatus 1 in the stand-alone image capturing mode. Since the captured data can be stored in the storage unit 23 of the radiographic image capturing apparatus 1, the console 58 is not required during the image capturing.

Thus, image capturing in sites such as the home of the patient, a disaster site, and an emergency care site, and image capturing of animals can be performed with only the radiographic image capturing apparatus 1 and a portable radiation source. This minimizes the number of devices required at the site. In a case where a small number of images are to be urgently captured to compensate for a missing or unsatisfactory image, only the radiographic image capturing apparatus 1 and a portable radiation source are required at the site of image capturing. Thus, the radiographic image capturing apparatus 1 is easy to use by the operator or radiologist.

[Detailed Configurational Example of Establishment of Correspondence]

If the image capturing mode of the radiographic image capturing apparatus 1 is switched to the stand-alone mode, the medical worker or radiologist should manually establish correspondence between the capturing order information and the radiographic images p. Some detailed configurational examples that readily establish correct correspondence will now be described.

The establishment of correspondence between the capturing order information and the radiographic images p with the console 58, such as in the configurational example A, will now be described. The following description also includes a case in which the correspondence appears on the display unit of the radiographic image capturing apparatus 1 or the display unit 71 of the portable information terminal 70, as described in the configuration example B.

Configurational Example 1

When the control unit 22 of the radiographic image capturing apparatus 1 captures the images in the stand-alone mode and stores the image data D and/or the data on the radiographic images p in the storage unit 23 of the radiographic image capturing apparatus 1 (see FIG. 2), identification information, i.e. IDs such as 1, 2, and so on, incremented for each image capturing is added to the respective pieces of data. During the image capturing in the stand-alone mode, the operator or radiologist records the number, for example, 1, 2, and so on according to the order of the image capturing in an irradiation record, or records the number, for example, 1, 2, and so on according to the order of the image capturing as well as the details of the image capturing, including the name of the patient and the capturing site, in a notepad or the portable information terminal 70.

Figure 13:
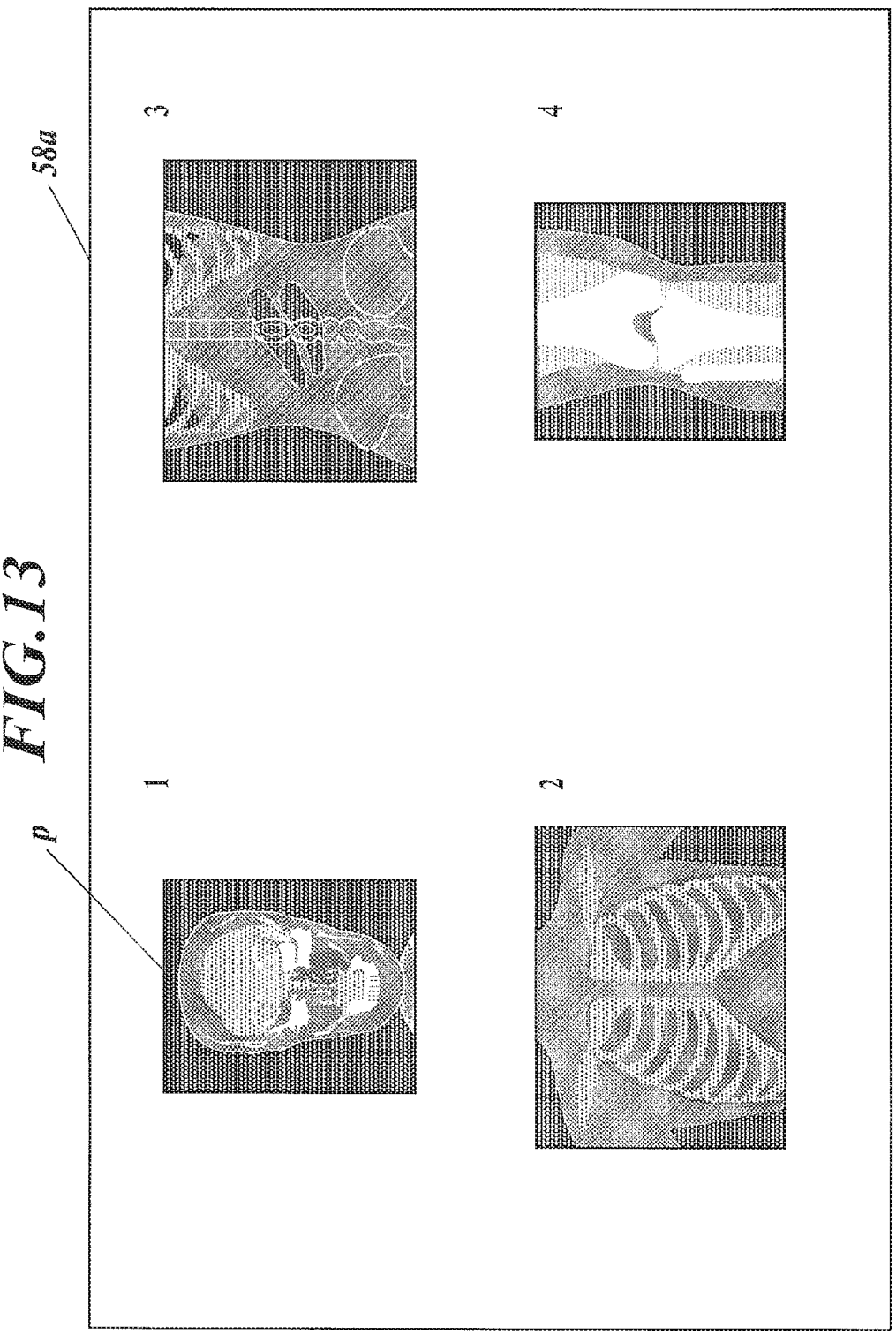
FIG. 13 illustrates thumbnails of radiographic images and the corresponding IDs appearing near the thumbnails on a display unit.

In the processing of correlating the radiographic images p with the capturing order information (Step S9 in FIG. 11 or 12), the console 58 may display thumbnails of the radiographic images p on the display unit 58a and IDs near the corresponding thumbnails, as illustrated in FIG. 13, for example.

The medical worker or radiologist can compare the thumbnails of the radiographic images p and/or the numbers as IDs displayed near the corresponding thumbnails with the numbers and/or the details of the image capturing recorded in the irradiation record, the notepad, or the portable information terminal 70 by the operator or radiologist, in such a configuration. Thus, the correspondence between the radiographic images p and the capturing order information can be readily and correctly established.

If the operator or radiologist fails an image capturing, the failed image capturing should also be assigned a number and written down, as in successful image capturing. The medical worker or radiologist can view the thumbnails of the radiographic images p (including the failed radiographic image) and the corresponding numbers as IDs on the display unit 58a of the console 58, to readily notice the failed image capturing, and to readily and correctly grasp the radiographic image p to be retaken corresponding to the failed image capturing.

Configurational Example 1-2

In the configurational example 1 described above, if the IDs (numbers) added to the data by the control unit 22 of the radiographic image capturing apparatus 1 do not match the number recorded by the operator or radiologist, the incorrect correspondence might be established between the radiographic images p and the capturing order information. Thus, a sounding unit, such as a speaker, may be provided in the radiographic image capturing apparatus 1, and the control unit 22 of the radiographic image capturing apparatus 1 may instruct the sounding unit to vocalize the IDs (numbers) added to the data so that the operator or radiologist can listen and record them.

Configurational Example 1-3

Although not illustrated, a label printer may be provided on the mobile medical cart 60 (see FIG. 8) or in the image capturing room R1 (see FIG. 3) to print out stickers including the information from the radiographic image capturing apparatus 1. The control unit 22 of the radiographic image capturing apparatus 1 sends the information on the IDs (numbers) added to the data to the label printer, and the label printer prints out stickers including the IDs (numbers) or barcodes corresponding to the IDs (numbers). The operator or radiologist attaches the sticker on which the IDs (numbers) or barcodes are printed to an irradiation record or a notepad.

The medical worker or radiologist may establish the correspondence between the radiographic images p and the capturing order information by comparing the IDs (numbers) displayed near the thumbnails with the IDs (numbers) attached to the irradiation report and the like or the IDs corresponding the barcodes read with a barcode reader. The configurational examples 1-2 and 1-3 also achieve the same advantageous effects as those of the configurational example 1-1.

Configurational Example 2

In place of the IDs and numbers in the configurational example 1 (including the configurational examples 1-2 and 1-3, the same hereinafter), the date and time of image capturing (the date and time of the reception of the radiation start signal from the radiation irradiating apparatus 57 or the date and time of the detection of the start of radiation irradiation), counted by a real-time clock (RTC) contained in the radiographic image capturing apparatus 1, may be added to the image data D and/or the data on the radiographic images p and stored. The operator or radiologist records the date and time of execution of a full-press operation of the exposure switch 56 of the radiation irradiating apparatus 57 as well as the details of image capturing in an irradiation record, a notepad, or the portable information terminal 70.

The date and time of image capturing may be displayed near each of the thumbnails of the radiographic images p displayed on the display unit 58a of the console 58 in the process of correlating the radiographic images p with the capturing order information, in place of the numbers of 1, 2, and so on, as illustrated in FIG. 13.

According to such a configuration, the medical worker or radiologist can compare the thumbnails of the radiographic images p and/or the date and time of image capturing displayed near the thumbnails with the date and time of image capturing and/or the details of the image capturing recorded in an irradiation record, a notepad, or the portable information terminal 70 by the operator or radiologist. Thus, correct correspondence between the radiographic images p and the capturing order information can be readily established. A failure in image capturing can be readily determines and the radiographic image p to be retaken corresponding to the failed image capturing can be readily and correctly identified, as in the configurational example 1.

Configurational Example 3

The date and time of image capturing measured by the RTC of the radiographic image capturing apparatus 1 is added to the image data D and/or the data on the radiographic images p, and the operator or radiologist records the date and time of execution of a full-press operation of the exposure switch 56 of the radiation irradiating apparatus 57 and the details of the image capturing in an irradiation record, a notepad, or the portable information terminal 70, as in the configurational example 2.

The interval between multiple image capturing operations performed on the same patient is shorter than that of image capturing operations performed on different patients, for example. Thus, the console 58 may calculate the interval between image capturing of a first image and image capturing of a second image on the basis of the date and time of image capturing added to the data (the image data D and/or the data on the radiographic images p). If the calculated interval is smaller than or equal to a predetermined threshold, such as three minutes, it can be determined that the data have been acquired through the image capturing of the same patient.

Figure 14:
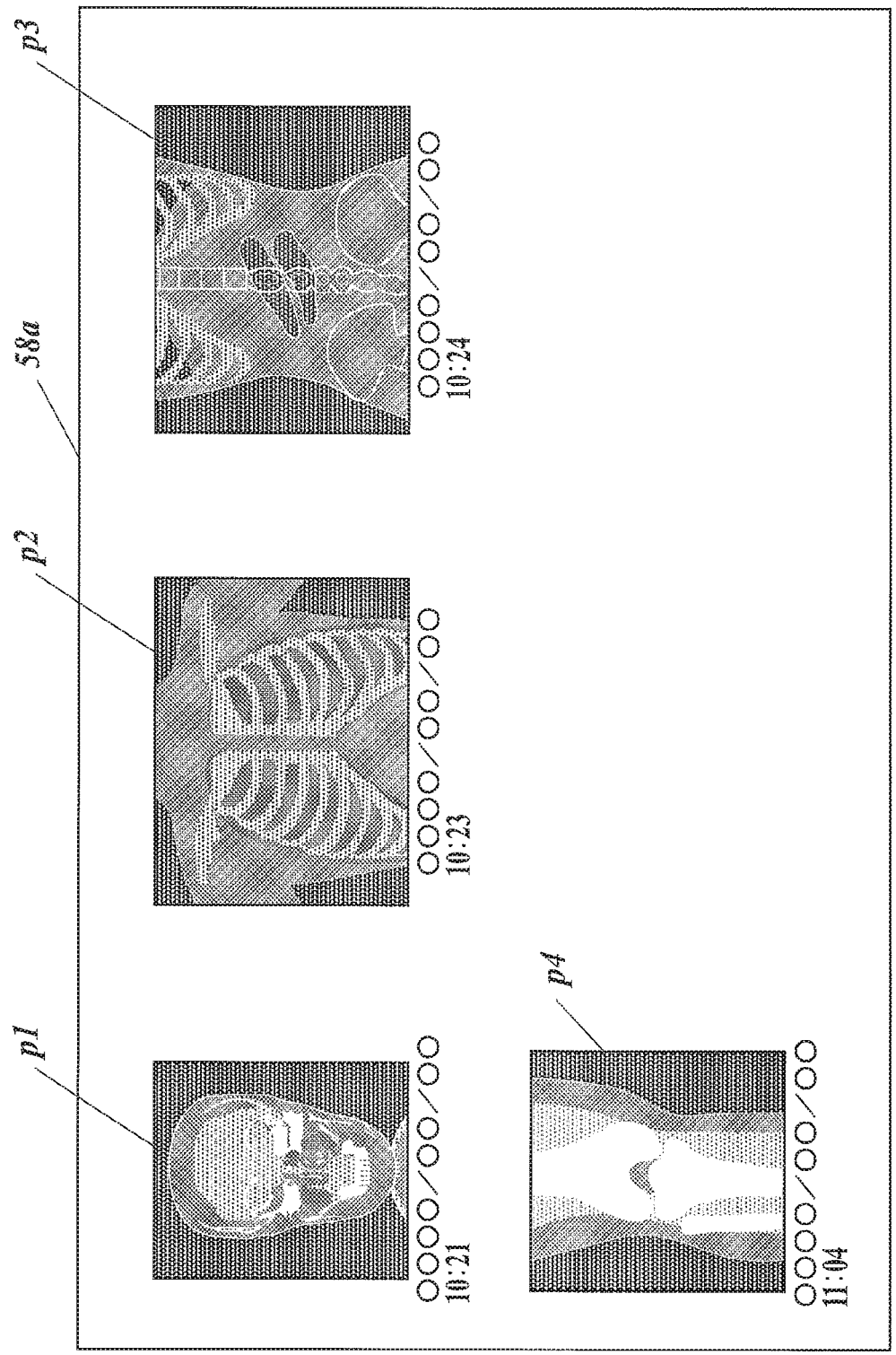
FIG. 14 illustrates a display of a group of radiographic images corresponding to a same patient.

The radiographic images p (p1 to p3 in FIG. 14) determined to be of the same patient may be separated from the radiographic image p (p4 in FIG. 14) determined to be of another patient such that the radiographic images p of the same patient are displayed in the same group, as illustrated in FIG. 14, for example.

According to such a configuration, the same advantageous effects are achieved as the configurational examples 1 and 2, and the medical worker or radiologist can readily establish the correct correspondence between the radiographic images p and the capturing order information without misidentifying the patients.

FIG. 14 illustrates thumbnails of the radiographic images p in the same group vertically arrayed. The images in the same group may be indicated in any other way. Although not illustrated, an example of such indication may include disposing the thumbnails of the radiographic images p in the same group in a box. The group of radiographic images p of the same patient may be indicated in any way.

Configurational Example 4

If the same site of the body of a hospitalized patient or a patient to be monitored is to be periodically captured, the capture radiographic image p is usually similar to the radiographic image p captured in the previous image capturing. Thus, the console 58 can identify the patient who is the subject of the current radiographic images p through comparison of the current radiographic image p and a radiographic image p captured within a predetermined period, such as within a month.

Although not illustrated, the console 58 may display the name of the identified patient near the thumbnails of the radiographic images p on the display unit 58a during establishment of the correspondence between the radiographic images p and the capturing order information, for example.

According to such a configuration, the medical worker or radiologist can compare the thumbnails of the radiographic images p and/or the name of the patient displayed near the thumbnails with the name of the patient assigned in the capturing order information and/or the details of the image capturing, to readily establish the correct correspondence between the radiographic images p and the capturing order information.

Configurational Example 5

As described above, a GPS may be provided in the radiographic image capturing apparatus 1 to measure the latitude and longitude of the radiographic image capturing apparatus 1, and the image capturing mode of the radiographic image capturing apparatus 1 can be switched (between the controlled mode and the stand-alone mode), depending on whether the radiographic image capturing apparatus 1 resides inside or outside the facility such as a hospital, on the basis of the measured latitude and longitude.

The control unit 22 of the radiographic image capturing apparatus 1 may use this technique to add information on the image capturing location (the latitude and longitude of the radiographic image capturing apparatus 1 at the time of reception of a radiation start signal from the radiation irradiating apparatus 57 or the latitude and longitude of the radiographic image capturing apparatus 1 at the time of detection of the start of radiation irradiation, for example) to the data and store them. The information on the latitude and longitude of the homes of patients is preliminarily input to the console 58.

Although not illustrated, in the process of correlating the radiographic images p with the capturing order information, the console 58 may identify a patient who is the capture subject of the radiographic images p corresponding to the thumbnails displayed on the display unit 58a on the basis of the information on the latitude and longitude added to the radiographic images p or the information on the latitude and longitude of the address of the home of the patient, and display the name of the identified patient near the thumbnails of the radiographic images p.

According to such a configuration, the medical worker or radiologist may compare the thumbnails of the radiographic images p and/or the name of the patient displayed near the thumbnails with the name of the patient assigned in the capturing order information and/or the details of the image capturing, to readily establish the correct correspondence between the radiographic images p and the capturing order information, as in the configurational example 4.

Instead of identification of a patient on the basis of the information on the latitude and longitude, a patient may be identified on the basis of information such as an address determined by the latitude and longitude. Thus, information other than latitude and longitude may be used.

Configurational Example 6

If image capturing is performed to a hospitalized patient in a hospital room R3 in a facility such as a hospital (see FIG. 8), the radiographic image capturing apparatus 1 may transmit/receive signals to/from an access point AP provided in the facility, and determine the location of the radiographic image capturing apparatus 1 in the facility on the basis of the intensity of the radio waves, to identify the patient who is the subject of image capturing.

Figure 15:
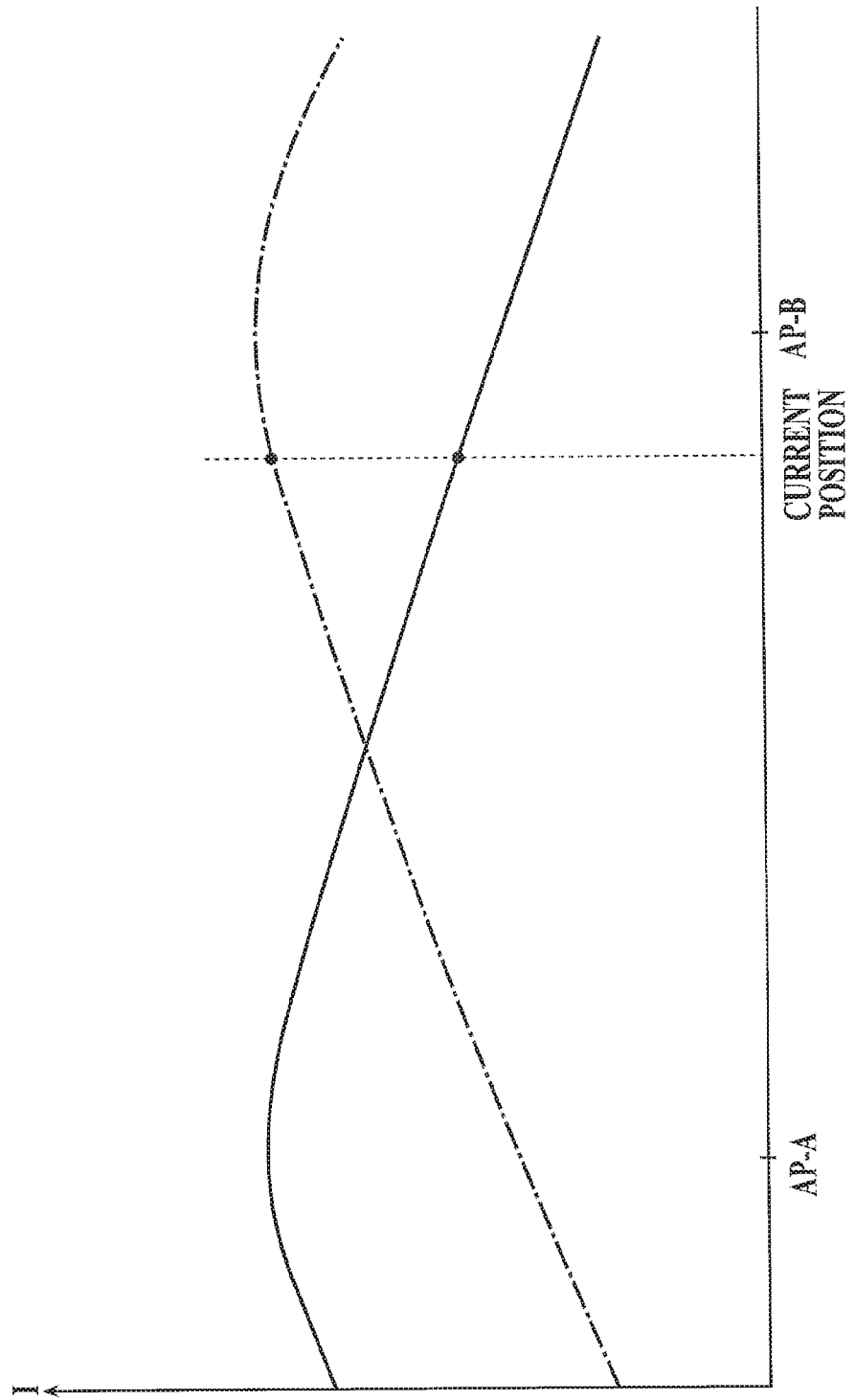
FIG. 15 illustrates the relation between the position of the radiographic image capturing apparatus and a radio wave intensity between the radiographic image capturing apparatus and each access point.

If multiple access points AP are provided in the facility, the intensities I of radio waves between the radiographic image capturing apparatus 1 and the respective access points AP vary depending on the distances between the current location of the radiographic image capturing apparatus 1 and the respective access points AP, as illustrated in FIG. 15. In the case illustrated in FIG. 15, the location of the radiographic image capturing apparatus 1 can be determined on the basis of the intensities I of the radio waves between the radiographic image capturing apparatus 1 and the respective access points AP-A and AP-B measured by the communication device 30 of the radiographic image capturing apparatus 1 (see FIG. 2), and/or the ratio of the intensity I of radio waves between the radiographic image capturing apparatus 1 and the access point AP-A to the intensity I of radio waves between the radiographic image capturing apparatus 1 and the access point AP-B, thereby identify the hospital room R3 under image capturing.

The control unit 22 of the radiographic image capturing apparatus 1 may preliminarily store a lookup table where the intensities I of radio waves between the radiographic image capturing apparatus 1 and the respective access points AP or the ratio of the intensity I of radio waves are correlated to the hospital room R3, and determine the hospital room R3 under the image capturing on the basis of the intensities I of radio waves between the radiographic image capturing apparatus 1 and the respective access points AP measured by the communication device 30 or the ratio thereof at the time of image capturing (the time of reception of a radiation start signal from the radiation irradiating apparatus 57 or the time of detection of the start of radiation irradiation). The identification information on the determined hospital room R3 is added to the data before storing the data in the storage unit 23.

Although not illustrated, the console 58 may display the identification information on the hospital room R3 added to the radiographic images p and the name of the hospital room R3 identified on the basis of the identification information, near the thumbnails of the radiographic images p displayed on the display unit 58a, during establishment of the correspondence between the radiographic images p and the capturing order information.

The medical worker or radiologist may identify the patient who is the subject of image capturing on the basis of the thumbnails of the radiographic images p and/or the identification information or name of the hospital room R3 displayed near the thumbnails, to readily establish the correct correspondence between the radiographic images p and the capturing order information, in such a configuration.

The control unit 22 of the radiographic image capturing apparatus 1 may preliminarily store map information of the facility such as a hospital, and identify the hospital room R3 under image capturing on the basis of the map information and the intensities I of radio wave between the radiographic image capturing apparatus 1 and the respective access points AP measured by the communication device 30 during image capturing or the ratio of the intensities I of radio wave. Alternatively, the hospital room R3 in which image capturing has been executed may be identified on the basis of the intensities I of radio waves between the radiographic image capturing apparatus and the respective access points AP through any other scheme.

Configurational Example 7

In clinical practice, the names of patients are confirmed to prevent misidentification of patients. Although not illustrated, a microphone may be provided in the radiographic image capturing apparatus 1. The voice of the operator or radiologist calling the name of a patient or the voice of a patient uttering his or her name may be recorded with the microphone in the radiographic image capturing apparatus 1, and the recorded audio information may be added to the data stored in the storage unit 23 of the radiographic image capturing apparatus 1.

The console 58 may be configured to play the audio information attached to the radiographic images p in response to assignment of a thumbnail by the medical worker or radiologist clicking one of the thumbnails corresponding to the radiographic images p displayed on the display unit 58a during establishment of the correspondence between the radiographic images p and the capturing order information.

The medial worker or radiologist can identify the patient who is the subject of image capturing on the basis of the thumbnails of the radiographic images p and/or the played audio signal, to readily establish the correct correspondence between the radiographic images p corresponding to the thumbnails and the capturing order information, in such a configuration.

The console 58 may identify the name of the patient through audio recognition of the audio information attached to the data and retrieve the capturing order information containing the determined name of the patient, to automatically establish the correspondence between the radiographic images p corresponding to the thumbnails and the capturing order information. The medical worker or radiologist should confirm the correspondence in such a configuration.

Configurational Example 8

Information such as a patient ID or the name of the patient (in the form of numbers, characters or a barcode) may be preliminarily printed on an irradiation record (e.g., on the margins of the irradiation record) prepared for each image capturing with a printer with transmissive or color ink (such as titanium ink) having a radiation transmittance different from that of the irradiation record. Image capturing may be performed with the irradiation record disposed between the incident surface R of radiation of the radiographic image capturing apparatus 1 (see FIG. 1) and the subject, so that the patient ID printed on the irradiation record is captured in the radiographic image p.

The position of the irradiation record relative to the subject and the radiographic image capturing apparatus 1 is adjusted such that the patient ID appear in the margins of the radiographic image p and does not overlap the subject or affected site. In such the case, an irradiation-record holder composed of a material that has no effect on the transmission of radiation, such as plastic, may be disposed on the incident surface R of the radiographic image capturing apparatus 1, and the irradiation record may be placed in the holder. This certainly prevents the irradiation record from being misaligned with the incident surface R of the radiographic image capturing apparatus 1 and failing to capture the patient ID in the radiographic image p or causing the patient ID to overlap the subject or affected site.

The medical worker or radiologist can readily establish the correct correspondence between the radiographic images p corresponding to the thumbnails and the capturing order information on the basis of the patient ID captured in the thumbnails of the radiographic images p displayed on the display unit 58a of the console 58.

The console 58 may identify the patient ID captured in the radiographic images p through image analysis, for example, and automatically establish correspondence between the radiographic images p and the capturing order information. The medical worker or radiologist should confirm the correspondence in such a configuration.

In the configurational examples described above, the medical worker or radiologist can manually and readily establish correct correspondence between the capturing order information and the radiographic images p, such manual establishment required after switch of the image capturing mode of the radiographic image capturing apparatus 1 to the stand-alone mode.

[Management of Data Captured in Stand-Alone Mode and Controlled Mode]

The radiographic image capturing apparatus 1 described above usually attaches IDs to the respective pieces of data (the image data D or the data on the radiographic image p) captured in every image capturing in either the stand-alone mode or the controlled mode, and manages the data. If IDs are simply attached to the data in the order of image capturing while the image capturing mode of the radiographic image capturing apparatus 1 switches between the stand-alone mode and the controlled mode, the IDs will not represent the image capturing mode in which the data has been captured, and thus the image capturing mode in which the data has been captured cannot be determined as either the stand-alone mode or the controlled mode by simply confirming the ID.

The image capturing mode of the data can be determined to be either the stand-alone mode or the controlled mode through the ingenious method of attaching IDs to the data as described below.

The control unit 22 of the radiographic image capturing apparatus 1 may reset the increment of the IDs attached to the data so that the IDs are recounted from one at every switch of the image capturing mode of the radiographic image capturing apparatus. For example, if the image capturing mode switches to the controlled mode to capture ten images, the stand-alone mode to capture three images, and then the controlled mode to continue image capturing, the IDs attached to the data will be numbered as . . . 8, 9, 10, 1, 2, 3, 1, 2, and 3 . . .

In this case, whether the data has been captured in the stand-alone mode or the controlled mode can be determined on the basis of the alignment sequence of the IDs and/or the number of images captured in each stand-alone mode. If the date and time of image capturing is attached to the data in addition to the IDs, the image capturing mode of the data can be more certainly determined to be either the stand-alone mode or the controlled mode.

In place of reset of the IDs to be attached to the data upon switch of the image capturing mode of the radiographic image capturing apparatus 1 as described above, the IDs can be incremented by a predetermined number, such 100 or 1000, and attached to the data upon switch of the image capturing mode.

The IDs to be attached to the data can be incremented by 100, for example, at every switch of the image capturing mode. If the image capturing mode switches to the controlled mode to capture ten images, the stand-alone mode to capture three images, and then the controlled mode to continue the image capturing, the IDs attached to the image data will be numbered as . . . 8, 9, 10, 101, 102, 103, 201, 202, and 203 . . .

Also by such a configuration, whether the data has been captured in the stand-alone mode or the controlled mode can be correctly determined on the basis of the order of the IDs and/or the number of images captured in the stand-alone mode.

Alternatively, the numbering rule of the IDs to be attached to the data can be modified at the time of switching the image capturing mode of the radiographic image capturing apparatus 1 as described above. Incremented IDs in the form of "A000XX" may be attached to the data captured in the stand-alone mode, and incremented IDs in the forms of "S000XX" may be attached to the data captured in the controlled mode, for example.

The image capturing mode of data can be correctly determined to be either the stand-alone mode or the controlled mode by merely confirming the IDs attached to the data in such a configuration. If the date and time of image capturing is attached to the data in addition to the IDs, as described above, the image capturing mode of the image capturing can be more certainly determined to be either the stand-alone mode or the controlled mode.

[Image Capturing with Multiple Radiographic Image Capturing Apparatuses]

The image capturing in the embodiments and configurational examples described above may be performed with multiple radiographic image capturing apparatuses 1. Individual switching of the image capturing modes of the radiographic image capturing apparatuses 1 results in some of the radiographic image capturing apparatuses 1 being in the stand-alone mode and the others in the controlled mode.

Such a state complicates discrimination between the controlled mode and the stand-alone mode of the radiographic image capturing apparatus 1 at any time point and identification of the radiographic image p (or the radiographic image capturing apparatus 1 capturing the radiographic image p) captured in the stand-alone mode of the radiographic image capturing apparatus 1 to be manually correlated with the capturing order information by the medical worker or radiologist. Thus, the medical worker or radiologist may establish incorrect correspondence or forget to establish the correspondence.

In image capturing with multiple radiographic image capturing apparatuses 1, when the image capturing mode of one of the apparatuses 1 is switched automatically or manually by the operator or radiologist to the stand-alone mode during the image capturing, the other radiographic image capturing apparatus(es) 1 preferably performs simultaneous switching of the image capturing mode to the stand-alone mode.

When the image capturing mode of one of the apparatuses 1 is switched automatically or manually by the operator or radiologist from the stand-alone mode to the controlled mode, the other radiographic image capturing apparatus(es) 1 preferably performs simultaneous switching of the image capturing mode to the controlled mode.

In such a configuration, determination of the duration of the stand-alone mode (i.e., the time entering the stand-alone mode to the time exiting the stand-alone mode) of one of the radiographic image capturing apparatuses 1 leads to the determination of the duration of the stand-alone mode of the other the radiographic image capturing apparatus(es) 1 used for image capturing. Thus, the medical worker or radiologist may confirm the information on the time of image capturing attached to the radiographic images p, to determine whether manual establishment of the radiographic images p and the capturing order information is necessary. In this way, the medical worker or radiologist can establish correct correspondence between the radiographic images p and the capturing order information without failure.

Also in this case, a notification for the simultaneous switch of the image capturing modes of all the radiographic image capturing apparatuses 1 may be provided to the operator or radiologist before the actual switch between the controlled mode and the stand-alone mode of the radiographic image capturing apparatus 1, and the image capturing mode of all the radiographic image capturing apparatuses 1 may switch only if the operator or radiologist performs the input operation to give permission for the switch.

The above embodiments should not be construed to limit the present invention and may be appropriately modified within the gist of the present invention.

INDUSTRIAL APPLICABILITY

The present invention can be applied to a field (a medical field, in particular) employing radiographic capturing.

REFERENCE SIGNS LIST

1 radiographic image capturing apparatus
7 radiation detecting element
22 control unit
23 storage unit
27 connector
29 antenna
50 radiographic image capturing system
51b, 55a connector residing in image capturing room
53 access point
58 console
D image data
p radiographic image
R1 image capturing room
R3 hospital room

The invention claimed is:
1. A radiographic image capturing apparatus comprising:
a two-dimensional array of radiation detecting elements that generate one or more electric charges in proportion to a dose of incident radiation; and
a controller that performs control, at least, to read the electric charges from the radiation detecting elements and generate image data, wherein
an image capturing mode is switchable between a controlled mode in which the radiographic image capturing apparatus is under control of an external capturing control device and a stand-alone mode in which the radiographic image capturing apparatus autonomously performs image capturing without the control of the capturing control device,
when the image capturing mode is switched to the controlled mode, the controller performs the control according to an instruction of the external capturing control device, and when the image capturing mode is switched to the stand-alone mode, the controller performs a process according to an instruction of a device other than the external capturing control device, the process being different from a process performed in the controlled mode,
in the controlled mode, the controller sends the image data read from the radiation detecting elements or radiographic image data after image correction of the image data, to the capturing control device, immediately after image capturing, and
in the stand-alone mode, the controller stores the image data read from the radiation detecting elements or the radiographic image data in a storage unit after the image capturing and sends the image data or the radiographic image data to the capturing control device or an external system upon establishment of wireless or wired connection with the capturing control device or the external system.

2. The radiographic image capturing apparatus of claim 1, wherein the controller automatically switches the image capturing mode to an image capturing mode suitable for a use environment of the radiographic image capturing apparatus.

3. The radiographic image capturing apparatus of claim 2, wherein the controller switches the image capturing mode from the stand-alone mode to the controlled mode when the radiographic image capturing apparatus is used in an image capturing room.

4. The radiographic image capturing apparatus of claim 1, wherein the controller switches the image capturing mode from the stand-alone mode to the controlled mode when a connector of the radiographic image capturing apparatus is connected to a connector residing in the image capturing room.

5. The radiographic image capturing apparatus of claim 3, wherein the controller switches the image capturing mode from the stand-alone mode to the controlled mode when wireless communication between an antenna of the radiographic image capturing apparatus and an access point residing in the image capturing room is established.

6. The radiographic image capturing apparatus of claim 2, further comprising an antenna that enables wirelessly communicating with the capturing control device,
wherein the controller switches the image capturing mode from the controlled mode to the stand-alone mode when judging that a radio wave environment during wireless communication with the capturing control device via the antenna is deteriorated.

7. The radiographic image capturing apparatus of claim 6, wherein the controller provides a notification of switch of the image capturing mode from the controlled mode to the stand-alone mode before switching the image capturing mode to the stand-alone mode, and switches the image capturing mode from the controlled mode to the stand-alone mode upon reception of an input operation which gives permission for the switch.

8. The radiographic image capturing apparatus of claim 6, wherein the controller switches the image capturing mode from the stand-alone mode to the controlled mode when judging that the radio wave environment is improved.

9. The radiographic image capturing apparatus of claim 8, wherein the controller provides a notification of switch of the image capturing mode from the stand-alone mode to the controlled mode before switching the image capturing mode to the controlled mode, and switches the image capturing mode from the stand-alone mode to the controlled mode upon reception of an input operation which gives permission for the switch.

10. The radiographic image capturing apparatus of claim 2, further comprising a position measuring unit that measures a position of the radiographic image capturing apparatus or an altitude measuring unit that measures an altitude of the radiographic image capturing apparatus, wherein
the controller switches the image capturing mode from the controlled mode to the stand-alone mode when the controller determines that the radiographic image capturing apparatus resides outside a facility based on the position of the radiographic image capturing apparatus measured by the position measuring unit or determines that the radiographic image capturing apparatus is used in round on a patient in a hospital room based on the altitude of the radiographic image capturing apparatus measured by the altitude measuring unit.

11. A radiographic image capturing system comprising:
a radiographic image capturing apparatus comprising:
a two-dimensional array of radiation detecting elements that generate one or more electric charges in proportion to a dose of incident radiation; and
a controller that performs control, at least, to read the electric charges from the radiation detecting elements and generate image data; and
a capturing control device capable of controlling an operation of the radiographic image capturing apparatus, wherein
the radiographic image capturing apparatus is capable of switching an image capturing mode between a controlled mode in which the radiographic image capturing apparatus is under control of the capturing control device and a stand-alone mode in which the radiographic image capturing apparatus autonomously performs image capturing without the control of the capturing control device,
when the image capturing mode is switched to the controlled mode, the controller performs the control according to an instruction of the external capturing control device, and when the image capturing mode is switched to the stand-alone mode, the controller performs a process according to an instruction of a device other than the external capturing control device, the process being different from a process performed in the controlled mode,
in the controlled mode, the controller sends the image data read from the radiation detecting elements or radiographic image data after image correction of the image data, to the capturing control device, immediately after image capturing, and
in the stand-alone mode, the controller stores the image data read from the radiation detecting elements or the radiographic image data in a storage unit after the image capturing and sends the image data or the radiographic image data to the capturing control device or an external system upon establishment of wireless or wired connection with the capturing control device or the external system.

\* \* \* \* \*